US012584179B2

(12) United States Patent　　　　　(10) Patent No.:　US 12,584,179 B2

Lopatin et al.　　　　　　　　　　　　(45) **Date of Patent:　　*Mar. 24, 2026**

(54) DNA METHYLATION AND MUTATIONAL ANALYSIS METHODS FOR BLADDER CANCER SURVEILLANCE

(71) Applicant: Genomic Health, Inc., Redwood City, CA (US)

(72) Inventors: Margarita Lopatin, Palo Alto, CA (US); Athanasios Tsiatis, San Francisco, CA (US); Christopher N. Silk, Redwood City, CA (US); David P. Miller, Albany, CA (US); Michael R. Crager, Menlo Park, CA (US); Phillip Febbo, Mill Valley, CA (US); Dejan Knezevic, Redwood City, CA (US)

(73) Assignee: Genomic Health, Inc., Redwood City, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 18/130,547

(22) Filed: Apr. 4, 2023

(65) Prior Publication Data

US 2023/0374604 A1　　　Nov. 23, 2023

Related U.S. Application Data

(63) Continuation of application No. 16/612,926, filed as application No. PCT/US2018/033146 on May 17, 2018, now Pat. No. 11,649,506.

(60) Provisional application No. 62/508,274, filed on May 18, 2017.

(51) Int. Cl.
　　*C12Q 1/68*　　　　(2018.01)
　　*A61P 35/00*　　　(2006.01)
　　*C07H 21/04*　　　(2006.01)
　　*C12Q 1/6886*　　(2018.01)
(52) U.S. Cl.
　　CPC ............ *C12Q 1/6886* (2013.01); *A61P 35/00* (2018.01); *C12Q 2600/106* (2013.01); *C12Q 2600/154* (2013.01); *G01N 2800/52* (2013.01); *G01N 2800/56* (2013.01); *G01N 2800/7028* (2013.01)
(58) Field of Classification Search
　　None
　　See application file for complete search history.

(56) References Cited

U.S. PATENT DOCUMENTS 11,649,506 B2 *　5/2023　Lopatin ................ C12Q 1/6886 435/6.14
2016/0273053 A1　9/2016　Zwarthoff et al.

FOREIGN PATENT DOCUMENTS

| CN | 103417983 A | 12/2013 |
| WO | 2010123354 A2 | 10/2010 |
| WO | 2010149782 A1 | 12/2010 |
| WO | 2014085666 A1 | 6/2014 |
| WO | 2014183093 A1 | 11/2014 |
| WO | 2015116837 A1 | 8/2015 |
| WO | 2016207656 A1 | 12/2016 |

OTHER PUBLICATIONS

Infinium Human Methylation 450 BeadChip (Data Sheet: Epigenetics, 2012). (Year: 2012).*

Kandimalla et al. (Clinical Cancer Research vol. 19, No. 17, 4760-4769, Sep. 2013). (Year: 2013).*

Feber et al. (Clinical Epigenetics, vol. 9, No. 8, Jan. 31, 2017) (Year: 2017).*

Kandimalla et al., "A 3-plex methylation assay combined with the FGFR3 mutation assay sensitively detects recurrent bladder cancer in voided urine," Clin Cancer Res 19(17):4760-4769 (2013).

Anonymous "Illumina Infinium HumanMethylation 450 Bead Chip," p. 8231, retried from the internet: https://www.ebi.ac.uk/arrayexpress/files/A-MEXP-2255/A-MEXP-2255.adf.txt (2012).

Cheng et al. Human Pathology; 2011 ;42: 455-481.

Chung et al. Cancer Epidemiol Biomarkers Prev; 2011; 20(7): 1483-1491.

Communication issued in European Application No. 18729258.6, mailed Dec. 10, 2020, 9 pages.

International Search Report and Written Opinion issued in International Application No. PCT/US2018/033146, mailed Jul. 8, 2018, 17 pages.

Kessel et al. The Journal of Urology; 2016; 195; 601-607.

Olkhov-Mitsel et al., "Epigenome-Wide DNA Methylation Profiling Identifies Differential Methylation Biomarkers in High-Grade Bladder Cancer," Translational Oncology 10(2):168-177, 2017.

Payne et al. The Prostate; 2009; 69:1257-1269 (Review).

Reinert, Hindawi Publishing Corporation; Advances in Urology; 2012; Article ID 503271: p. 1-11.

Savio et al., "Tissue-Based DNA Methylation Profiling Establishes a Novel Panel of Biomarkers for Discrimination of High-Grade Versus Low-Grade Bladder Cancer," Journal of Urology 193(4S):e860, 2015.

Scher et al. The Journal of Urology; 2012; vol. 188: 2101-2107.

Tilley (Dissertation "Analysis of Bladder Cancer Tumor CPG Methylation and Gene Expression Within the Cancer Genome Atlas Identifies GRIA1 as a Prognostic Biomarker for Basal-Like Bladder Cancer", Chapel Hill, NC, Ingested to the repository on Jul. 5, 2017) (2017).

Van Kessel et al., "Validation of a DNA Methylation-Mutation Urine Assay to Select Patients with Hematuria for Cystoscopy," Journal of Urology 197(3):590-595, 2017.

Zhang et al. Genome Biology; 2015; 16; 14: 1-19.

Zhao et al. PLOS One; 2012; 7; 4: e35175: p. 1-12.

USPTO file history of U.S. Appl. No. 16/612,926, filed Nov. 12, 2019.

* cited by examiner

*Primary Examiner* — Jeanine A Goldberg

(74) *Attorney, Agent, or Firm* — McNeill PLLC

(57) ABSTRACT

The present disclosure relates to methods of monitoring bladder cancer patients and analyzing patient samples for presence of methylated DNA and optionally particular gene mutations. In some embodiments, analysis results are correlated with clinical outcome measures such as risk of bladder cancer recurrence.

19 Claims, 17 Drawing Sheets

DNA METHYLATION AND MUTATIONAL ANALYSIS METHODS FOR BLADDER CANCER SURVEILLANCE

CROSS-REFERENCE TO RELATED APPLICATIONS

This application is a continuation of U.S. application Ser. No. 16/612,926, filed Nov. 12, 2019, which is a national phase entry pursuant to 35 U.S.C. § 371 of International Application No. PCT/US2018/033146, filed May 17, 2018, which claims the benefit of priority of U.S. Provisional Application No. 62/508,274, filed May 18, 2017, each of which is incorporated by reference herein in its entirety for any purpose.

TECHNICAL FIELD

The present disclosure relates to methods of monitoring bladder cancer patients and analyzing patient samples for presence of methylated DNA and optionally particular gene mutations. In some embodiments, analysis results are correlated with clinical outcome measures such as risk of bladder cancer recurrence.

INTRODUCTION

Bladder cancer is one of the most common cancers in industrialized countries and is one of the costliest cancers to diagnose and monitor. (See R. Siegel et al., *CA Cancer J Clin* 63: 11-30 (2013); and see, e.g., T. Reinert Adv. *Urol.*, Article ID 503271, doi:10.1155/2012/503271, pp. 1-11 (2012); see also A. Feber et al., *Clin. Epigenetics* 9:8 doi: 10.1186/s13148-016-0303-5 (2017)). For example, the large majority of new cases present as non-muscle invasive bladder cancer, with a low probability of metastasis, but there remains potential for progression to a more aggressive disease (e.g., high grade, muscle invasive) and monitoring patients for development of more aggressive forms of the disease requires frequent surveillance involving expensive and invasive cystoscopy procedures over a fairly long period of time (e.g., 5 years or more). (See, e.g., M. Babjuk et al. *Eur. Urol.* 59: 997-1008 (2011); B. W. van Rhijn et al., *Eur. Urol.* 56: 430-42 (2009); M. F. Botteman et al., *Pharmacoeconomics* 21: 1315-30 (2003).) Cystoscopy, for instance, may be performed in some patients for initial diagnosis and then subsequently three months after surgical treatment and, if negative, then after intervals of 9 months to 1 year for the next 5 years. In certain high risk patients, cystoscopy may be performed every 3 months for up to 2 years post-surgery, every 6 months for the subsequent 3 years, and then annually thereafter. (See Reinert, page 1.) Thus, noninvasive diagnostic tests may be helpful, for example, as additions to cystoscopy during this active surveillance treatment period, as they may provide further information regarding the status of a patient's risk of recurrence. One goal for diagnostic testing in bladder cancer is also to allow for cystoscopy tests to be eliminated or reduced in frequency during active surveillance.

Previous studies have indicated that DNA methylation, in which a methyl group is added to the $5^{th}$ carbon in cytosine in a CpG dinucleotide stretch, may occur inside gene coding sequences, as well as in so-called CpG islands in the human genome. Generally, CpG dinucleotides in CpG islands are unmethylated in normal cells whereas CpG dinucleotides found in isolated sequence stretches in gene coding regions may be methylated in normal cells. The CpG dinucleotides outside of the CpG island regions may be significantly less methylated in cancer cells compared to normal cells. (See Reinert at page 4.) Several studies have shown that bladder cancer cells "leak" DNA into urine and that this DNA can be detected by looking at methylation of genes in urine samples. (Id. at pages 4-5, Table 3.) The present disclosure describes gene sets and algorithms for assessing risk of recurrence in bladder cancer patients from examination of DNA methylation as well as presence of gene mutations from urine sediment samples.

SUMMARY

This application discloses methods of monitoring patients with bladder cancer, comprising, for example, obtaining a urine sediment sample from a patient; bisulfite converting DNA from the sample; performing methylation-specific quantitative PCR on the bisulfite converted DNA to determine the amount and/or the concentration of methylated DNA in the sample from a set of genes comprising at least four genes selected from MEIS1, NKPD1, ONECUT2, KLF2, OSR1, SOX1, EOMES, DDX25, and TMEM106A and from at least one reference gene. In some embodiments, the patient has been diagnosed with non-muscle-invasive bladder cancer. In some embodiments, the patient's tumor has previously been diagnosed as Ta, Tis, T0, or low grade. In some embodiments, the patient's tumor has previously been diagnosed as T1 or high grade. In some embodiments, the patient has been diagnosed with muscle-invasive bladder cancer. In some embodiments, the method is conducted prior to cystoscopy. In some embodiments, the method is conducted after a negative cystoscopy. In some embodiments, the method is conducted at least once per year, such as once per six months, or once per three months, for example, as part of an active surveillance visit.

In some embodiments, at least four genes comprise MEIS1, NKPD1, ONECUT2, and KLF2. In some embodiments, the reference genes comprise one or more of CTNS, TOP3A, COL2A and SLC24A3. In some embodiments, the set of genes further comprises at least one gene selected from EPHX3, IRX5, NID2, VIM, and ITPKB. In some embodiments, the set of genes comprises one of the following gene sets along with at least one reference gene: (a) M1: MEIS1, NKPD1, ONECUT2, KLF2; (b) M2: MEIS1, NKPD1, ONECUT2, OSR1; (c) M3: MEIS1, NKPD1, KLF2, SOX1; (d) M4: ONECUT2, OSR1, SOX1, EOMES; (e) M5: MEIS1, NKPD1, ONECUT2, OSR1, TMEM106A; EPHX3; (f) M6: MEIS1, NKPD1, ONECUT2, KLF2, TMEM106A, IRX5; (g) M7: MEIS1, NKPD1, ONECUT2, KLF2, SOX1, TMEM106A; (h) M8: ONECUT2, OSR1, SOX1, EOMES, NID2, VIM; and (i) M9: MEIS1, NKPD1, ONECUT2, KLF2, TMEM106A, ITPKB. In some embodiments, the set of genes consists of one of the following gene sets: (a) M1: MEIS1, NKPD1, ONECUT2, KLF2, and at least one reference gene; (b) M2: MEIS1, NKPD1, ONECUT2, OSR1, and at least one reference gene; (c) M3: MEIS1, NKPD1, KLF2, SOX1, and at least one reference gene; (d) M4: ONECUT2, OSR1, SOX1, EOMES, and at least one reference gene; (e) M5: MEIS1, NKPD1, ONECUT2, OSR1, TMEM106A; EPHX3, and at least one reference gene; (f) M6: MEIS1, NKPD1, ONECUT2, KLF2, TMEM106A, IRX5, and at least one reference gene; (g) M7: MEIS1, NKPD1, ONECUT2, KLF2, SOX1, TMEM106A, and at least one reference gene; (h) M8: ONECUT2, OSR1, SOX1, EOMES, NID2, VIM, and at least one reference gene; and (i) M9: MEIS1, NKPD1, ONECUT2, KLF2, TMEM106A, ITPKB, and at least one reference gene.

In some embodiments, the methods further comprise determining a risk of recurrence for the patient or determining presence of an actual recurrence, comprising comparing the amount and/or concentration of methylation for the patient to the amount and/or concentration of methylation for a reference set of bladder cancer patients. In some embodiments, the patient has previously been diagnosed to be at low risk of recurrence and the method is conducted, for example, to confirm this diagnosis and/or to confirm the absence of any actual recurrence. In some embodiments, a patient has previously been determined to have a low risk of recurrence based on a Ta or low grade tumor sample comprising tissue from TURBT, cystoscopy, or from an upper GU workup. In some embodiments, the low risk patient has either normal or abnormal cystoscopy. In some embodiments, the low risk patient has either normal or abnormal cytology. In some embodiments, the patient has previously been diagnosed to be at high risk of recurrence and the method is conducted, for example, to confirm this diagnosis and to confirm the absence of any actual recurrence. For example, in some embodiments, a patient has previously been determined to have a high risk of recurrence based on a high grade, T1-T2, or Tis tumor sample comprising tissue from TURBT, cystoscopy, or from an upper GU workup. In some embodiments, the high risk patient has either normal or abnormal cystoscopy. In some embodiments, the high risk patient has either normal or abnormal cytology.

In some embodiments, the method further comprises analyzing the bisulfate converted DNA for mutations in one or both of FGFR3 and TERT. In some embodiments, the FGFR3 mutation is at chromosome position ch4:1803568 and the TERT mutation is at chromosome position chr5:1295228. In some embodiments, the method further comprises comparing the presence or absence of mutations in FGFR3 and/or TERT to the prevalence of the FGFR3 and TERT mutations in the reference set of bladder cancer patients.

The instant disclosure also concerns methods of treating a bladder cancer patient having a low risk of recurrence, comprising, for example, obtaining a urine sediment sample from the patient; bisulfite converting DNA from the sample; performing methylation-specific quantitative PCR on the bisulfite converted DNA to determine the amount and/or the concentration of methylated DNA in the sample from a set of genes comprising at least four genes selected from MEIS1, NKPD1, ONECUT2, KLF2, OSR1, SOX1, EOMES, DDX25, and TMEM106A and from at least one reference gene; determining that the patient has a low risk of recurrence by comparing the amount and/or concentration of methylation for the patient to the amount and/or concentration of methylation for a reference set of bladder cancer patients; and treating the patient with active surveillance. In some embodiments, the treatment with active surveillance comprises reducing the frequency of cystoscopy for the patient, for example, when the low risk status of the patient is confirmed by the method. In some embodiments, the patient has been diagnosed with non-muscle-invasive bladder cancer. In some embodiments, the patient's tumor has previously been diagnosed as Ta, Tis, T0, or low grade. In some embodiments, the patient's tumor has previously been diagnosed as T1 or high grade. In some embodiments, the method is conducted prior to cystoscopy. In some embodiments, the method is conducted after a negative cystoscopy.

In some embodiments of the above treatment methods, at least four genes comprise MEIS1, NKPD1, ONECUT2, and KLF2. In some embodiments, the reference genes comprise one or more of CTNS, TOP3A, COL2A and SLC24A3. In some embodiments, the set of genes further comprises at least one gene selected from EPHX3, IRX5, NID2, VIM, and ITPKB. In some embodiments, the set of genes comprises one of the following gene sets along with at least one reference gene: (a) M1: MEIS1, NKPD1, ONECUT2, KLF2; (b) M2: MEIS1, NKPD1, ONECUT2, OSR1; (c) M3: MEIS1, NKPD1, KLF2, SOX1; (d) M4: ONECUT2, OSR1, SOX1, EOMES; (e) M5: MEIS1, NKPD1, ONECUT2, OSR1, TMEM106A; EPHX3; (f) M6: MEIS1, NKPD1, ONECUT2, KLF2, TMEM106A, IRX5; (g) M7: MEIS1, NKPD1, ONECUT2, KLF2, SOX1, TMEM106A; (h) M8: ONECUT2, OSR1, SOX1, EOMES, NID2, VIM; and (i) M9: MEIS1, NKPD1, ONECUT2, KLF2, TMEM106A, ITPKB. In some embodiments, the set of genes consists of one of the following gene sets: (a) M1: MEIS1, NKPD1, ONECUT2, KLF2, and at least one reference gene; (b) M2: MEIS1, NKPD1, ONECUT2, OSR1, and at least one reference gene; (c) M3: MEIS1, NKPD1, KLF2, SOX1, and at least one reference gene; (d) M4: ONECUT2, OSR1, SOX1, EOMES, and at least one reference gene; (e) M5: MEIS1, NKPD1, ONECUT2, OSR1, TMEM106A; EPHX3, and at least one reference gene; (f) M6: MEIS1, NKPD1, ONECUT2, KLF2, TMEM106A, IRX5, and at least one reference gene; (g) M7: MEIS1, NKPD1, ONECUT2, KLF2, SOX1, TMEM106A, and at least one reference gene; (h) M8: ONECUT2, OSR1, SOX1, EOMES, NID2, VIM, and at least one reference gene; and (i) M9: MEIS1, NKPD1, ONECUT2, KLF2, TMEM106A, ITPKB, and at least one reference gene. In some embodiments, the method further comprises analyzing the bisulfate converted DNA for mutations in one or both of FGFR3 and TERT. In some embodiments, the FGFR3 mutation is at chromosome position ch4:1803568 and the TERT mutation is at chromosome position chr5:1295228. In some embodiments, the method further comprises comparing the presence or absence of mutations in FGFR3 and/or TERT to that of the reference set of bladder cancer patients.

The instant disclosure also relates to systems for quantifying DNA methylation in a urine sediment sample from a bladder cancer patient. In some embodiments, the systems may comprise (a) at least one cartridge with at least one well, the at least one well comprising primers for amplification of bisulfite modified DNA of at least four genes selected from MEIS1, NKPD1, ONECUT2, KLF2, OSR1, SOX1, EOMES, DDX25, and TMEM106A, and at least one reference gene, wherein the cartridge is configured for performance of methylation-specific quantitative PCR on the genes, and wherein the primers are optionally attached to the at least one well; (b) a detection device for detecting amplified DNA from each gene; and (c) computer software for quantifying the amount and/or concentration of methylated DNA from the genes, wherein the software optionally compares the amount and/or concentration of methylation for the patient to the amount and/or concentration of methylation for a reference set of bladder cancer patients. In some embodiments, the cartridge is configured for performance of methylation-specific quantitative PCR on a set of genes comprising MEIS1, NKPD1, ONECUT2, and KLF2, and at least one reference gene. In some embodiments, the cartridge is configured for performance of methylation-specific quantitative PCR on a set of genes comprising MEIS1, NKPD1, ONECUT2, and KLF2, and one or more of OSR1, SOX1, EOMES, DDX25, and TMEM106A, and at least one reference gene. In some embodiments, the cartridge is configured for performance of methylation-specific quantitative PCR on a set of genes comprising MEIS1, NKPD1, ONECUT2, and KLF2, and one or more of EPHX3, IRX5, NID2, VIM, and ITPKB, and at least one reference gene. In some embodiments, the cartridge is configured for performance of methylation-specific quantitative PCR on a set of genes comprising one of the following gene sets: (a) M1: MEIS1, NKPD1, ONECUT2, KLF2, and at least one reference gene; (b) M2: MEIS1, NKPD1, ONECUT2, OSR1, and at least one reference gene; (c) M3: MEIS1, NKPD1, KLF2, SOX1, and at least one reference gene; (d) M4: ONECUT2, OSR1, SOX1, EOMES, and at least one reference gene; (e) M5: MEIS1, NKPD1, ONECUT2, OSR1, TMEM106A; EPHX3, and at least one reference gene; (f) M6: MEIS1, NKPD1, ONECUT2, KLF2, TMEM106A, IRX5, and at least one reference gene; (g) M7: MEIS1, NKPD1, ONE-CUT2, KLF2, SOX1, TMEM106A, and at least one reference gene; (h) M8: ONECUT2, OSR1, SOX1, EOMES, NID2, VIM, and at least one reference gene; and (i) M9: MEIS1, NKPD1, ONECUT2, KLF2, TMEM106A, ITPKB, and at least one reference gene. In some embodiments, the cartridge is configured for performance of methylation-specific quantitative PCR on a set of genes consisting of one of the following gene sets: (a) M1: MEIS1, NKPD1, ONE-CUT2, KLF2, and at least one reference gene; (b) M2: MEIS1, NKPD1, ONECUT2, OSR1, and at least one reference gene; (c) M3: MEIS1, NKPD1, KLF2, SOX1, and at least one reference gene; (d) M4: ONECUT2, OSR1, SOX1, EOMES, and at least one reference gene; (e) M5: MEIS1, NKPD1, ONECUT2, OSR1, TMEM106A; EPHX3, and at least one reference gene; (f) M6: MEIS1, NKPD1, ONE-CUT2, KLF2, TMEM106A, IRX5, and at least one reference gene; (g) M7: MEIS1, NKPD1, ONECUT2, KLF2, SOX1, TMEM106A, and at least one reference gene; (h) M8: ONECUT2, OSR1, SOX1, EOMES, NID2, VIM, and at least one reference gene; and (i) M9: MEIS1, NKPD1, ONECUT2, KLF2, TMEM106A, ITPKB, and at least one reference gene. In some embodiments, the at least one reference gene comprises one or more of CTNS, TOP3A, COL2A and SLC24A3. In some embodiments, the primers are attached to the at least one well of the cartridge. In some embodiments, the cartridge further comprises reagents for detecting mutations in one or both of TERT and FGFR3. In some embodiments, the FGFR3 mutation is FGFR3 is a C to G substitution at chr4:1803568 and wherein the TERT mutation is a G to A substitution at chr5:1295228. In some embodiments, the system is capable of performing the above methods of methylation quantitation in a bladder cancer patient urine sediment sample.

The present disclosure also relates to cartridges comprising at least one well comprising primers for amplification of bisulfite modified DNA of at least four genes selected from MEIS1, NKPD1, ONECUT2, KLF2, OSR1, SOX1, EOMES, DDX25, and TMEM106A, and at least one reference gene, wherein the cartridge is configured for performance of methylation-specific quantitative PCR on the genes, and wherein the primers are optionally attached to the at least one well. The cartridges may be components of the above systems, or they may be independent of the above systems. For example, cartridges may be configured to work with a variety of detection apparatuses and systems. In some embodiments, the cartridge is configured for performance of methylation-specific quantitative PCR on a set of genes comprising MEIS1, NKPD1, ONECUT2, and KLF2, and at least one reference gene. In some embodiments, the set of genes comprises MEIS1, NKPD1, ONECUT2, and KLF2, and one or more of OSR1, SOX1, EOMES, DDX25, and TMEM106A, and at least one reference gene. In some embodiments, the set of genes comprises MEIS1, NKPD1, ONECUT2, and KLF2, and one or more of EPHX3, IRX5, NID2, VIM, and ITPKB, and at least one reference gene. In some embodiments, the cartridge is configured for performance of methylation-specific quantitative PCR on a set of genes comprising one of the following gene sets: (a) M1: MEIS1, NKPD1, ONECUT2, KLF2, and at least one reference gene; (b) M2: MEIS1, NKPD1, ONECUT2, OSR1, and at least one reference gene; (c) M3: MEIS1, NKPD1, KLF2, SOX1, and at least one reference gene; (d) M4: ONECUT2, OSR1, SOX1, EOMES, and at least one reference gene; (e) M5: MEIS1, NKPD1, ONECUT2, OSR1, TMEM106A; EPHX3, and at least one reference gene; (f) M6: MEIS1, NKPD1, ONECUT2, KLF2, TMEM106A, IRX5, and at least one reference gene; (g) M7: MEIS1, NKPD1, ONE-CUT2, KLF2, SOX1, TMEM106A, and at least one reference gene; (h) M8: ONECUT2, OSR1, SOX1, EOMES, NID2, VIM, and at least one reference gene; and (i) M9: MEIS1, NKPD1, ONECUT2, KLF2, TMEM106A, ITPKB, and at least one reference gene. In some embodiments, the cartridge is configured for performance of methylation-specific quantitative PCR on a set of genes consisting of one of the following gene sets: (a) M1: MEIS1, NKPD1, ONE-CUT2, KLF2, and at least one reference gene; (b) M2: MEIS1, NKPD1, ONECUT2, OSR1, and at least one reference gene; (c) M3: MEIS1, NKPD1, KLF2, SOX1, and at least one reference gene; (d) M4: ONECUT2, OSR1, SOX1, EOMES, and at least one reference gene; (e) M5: MEIS1, NKPD1, ONECUT2, OSR1, TMEM106A; EPHX3, and at least one reference gene; (f) M6: MEIS1, NKPD1, ONE-CUT2, KLF2, TMEM106A, IRX5, and at least one reference gene; (g) M7: MEIS1, NKPD1, ONECUT2, KLF2, SOX1, TMEM106A, and at least one reference gene; (h) M8: ONECUT2, OSR1, SOX1, EOMES, NID2, VIM, and at least one reference gene; and (i) M9: MEIS1, NKPD1, ONECUT2, KLF2, TMEM106A, ITPKB, and at least one reference gene. In some embodiments, the at least one reference gene comprises one or more of CTNS, TOP3A, COL2A and SLC24A3. In some embodiments, the primers are attached to the at least one well of the cartridge. In some embodiments, the cartridge further comprises reagents for detecting mutations in one or both of TERT and FGFR3. In some embodiments, the FGFR3 mutation is FGFR3 is a C to G substitution at chr4:1803568 and wherein the TERT mutation is a G to A substitution at chr5:1295228. The above cartridges may be used in the methods and systems further above.

The disclosure also contemplates kits comprising the cartridges described above. Kits may further comprise at least one of the following: (a) deoxyribonucleotide triphosphates dTTP, dATP, dCTP and dGTP; (b) at least one DNA polymerase enzyme; and (c) at least one reaction and/or wash buffer. The kits may, for example, be components of the systems described above and may be useful in performing the methods described earlier in this section. In some embodiments, the kits comprise each of (a) deoxyribonucleotide triphosphates dTTP, dATP, dCTP and dGTP; (b) at least one DNA polymerase enzyme; and (c) at least one reaction and/or wash buffer. In some embodiments, the kits further comprise at least one detection reagent. In some embodiments, the kits further comprise at least one reagent for bisulfite conversion of DNA. In some embodiments, the kits further comprise reagents for reagents for detecting mutations in one or both of TERT and FGFR3. In some such embodiments, the FGFR3 mutation is FGFR3 is a C to G substitution at chr4:1803568 and wherein the TERT mutation is a G to A substitution at chr5:1295228. The kits herein may further comprise instructions for use.

Also contemplated herein are compositions comprising a set of primers for PCR amplification of bisulfite modified DNA of at least four genes selected from MEIS1, NKPD1, ONECUT2, KLF2, OSR1, SOX1, EOMES, DDX25, and TMEM106A, and at least one reference gene. In some compositions, the set of primers is for a group of genes consisting of at least four genes selected from MEIS1, NKPD1, ONECUT2, KLF2, OSR1, SOX1, EOMES, DDX25, and TMEM106A, and at least one reference gene. In some compositions herein, the genes comprise MEIS1, NKPD1, ONECUT2, and KLF2, and at least one reference gene. In some compositions herein, the genes consist of MEIS1, NKPD1, ONECUT2, and KLF2, and at least one reference gene. In some compositions herein, the genes comprise MEIS1, NKPD1, ONECUT2, and KLF2, and one or more of OSR1, SOX1, EOMES, DDX25, and TMEM106A, and at least one reference gene. In some compositions herein, the genes consist of MEIS1, NKPD1, ONECUT2, and KLF2, and one or more of OSR1, SOX1, EOMES, DDX25, and TMEM106A, and at least one reference gene. In some compositions herein, the genes comprise MEIS1, NKPD1, ONECUT2, and KLF2, and one or more of EPHX3, IRX5, NID2, VIM, and ITPKB, and at least one reference gene. In some compositions herein, the genes consist of MEIS1, NKPD1, ONECUT2, and KLF2, and one or more of EPHX3, IRX5, NID2, VIM, and ITPKB, and at least one reference gene. Some compositions herein comprise a set of primers for methylation-specific quantitative PCR of a set of genes comprising: (a) MEIS1, NKPD1, ONECUT2, KLF2, and at least one reference gene; (b) MEIS1, NKPD1, ONECUT2, OSR1, and at least one reference gene; (c) MEIS1, NKPD1, KLF2, SOX1, and at least one reference gene; (d) ONECUT2, OSR1, SOX1, EOMES, and at least one reference gene; (e) MEIS1, NKPD1, ONECUT2, OSR1, TMEM106A; EPHX3, and at least one reference gene; (f) MEIS1, NKPD1, ONECUT2, KLF2, TMEM106A, IRX5, and at least one reference gene; (g) MEIS1, NKPD1, ONECUT2, KLF2, SOX1, TMEM106A, and at least one reference gene; (h) ONECUT2, OSR1, SOX1, EOMES, NID2, VIM, and at least one reference gene; or (i) MEIS1, NKPD1, ONECUT2, KLF2, TMEM106A, ITPKB, and at least one reference gene. Some compositions herein comprise a set of primers for methylation-specific quantitative PCR of a set of genes consisting of: (a) MEIS1, NKPD1, ONECUT2, KLF2, and at least one reference gene; (b) MEIS1, NKPD1, ONECUT2, OSR1, and at least one reference gene; (c) MEIS1, NKPD1, KLF2, SOX1, and at least one reference gene; (d) ONECUT2, OSR1, SOX1, EOMES, and at least one reference gene; (e) MEIS1, NKPD1, ONECUT2, OSR1, TMEM106A; EPHX3, and at least one reference gene; (f) MEIS1, NKPD1, ONECUT2, KLF2, TMEM106A, IRX5, and at least one reference gene; (g) MEIS1, NKPD1, ONECUT2, KLF2, SOX1, TMEM106A, and at least one reference gene; (h) ONECUT2, OSR1, SOX1, EOMES, NID2, VIM, and at least one reference gene; or (i) MEIS1, NKPD1, ONECUT2, KLF2, TMEM106A, ITPKB, and at least one reference gene. In some compositions herein, the at least one reference gene comprises one or more of CTNS, TOP3A, COL2A and SLC24A3. Some compositions herein further comprise reagents for detecting mutations in one or both of TERT and FGFR3. In some embodiments, the FGFR3 mutation is FGFR3 is a C to G substitution at chr4:1803568 and wherein the TERT mutation is a G to A substitution at chr5:1295228. Some compositions herein further comprising at least one of the following: (a) deoxyribonucleotide triphosphates dTTP, dATP, dCTP and dGTP; (b) at least one DNA polymerase enzyme; (c) at least one reaction and/or wash buffer. In some embodiments, the composition comprises each of (a) deoxyribonucleotide triphosphates dTTP, dATP, dCTP and dGTP; (b) at least one DNA polymerase enzyme; and (c) at least one reaction and/or wash buffer. In some embodiments, the composition further comprises at least one detection reagent. In some embodiments, the composition further comprises at least one reagent for bisulfite conversion of DNA. Compositions herein may further be components of the above-described systems, cartridges, and kits, and may be useful in the methods described earlier in this section.

Figure 7:
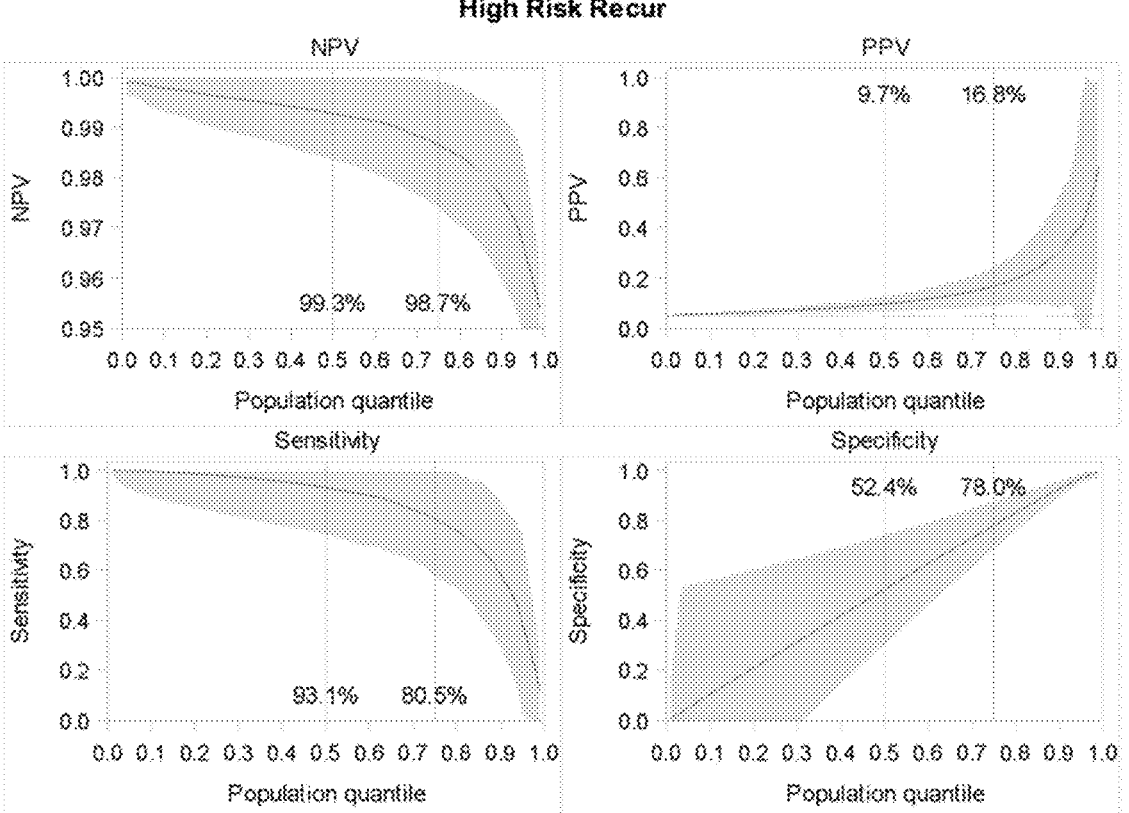
FIG. 7 provides a performance summary for the M1 plus mutation analysis of the concentration of methylated DNA for initial low risk of recurrence patients, as described in Example 3 below. Specifically, FIG. 1 provides negative predictive value (NPV), positive predictive value (PPV), sensitivity, and specificity data for predicting those low risk patients who are actually at high risk of recurrence.
Figure 8:
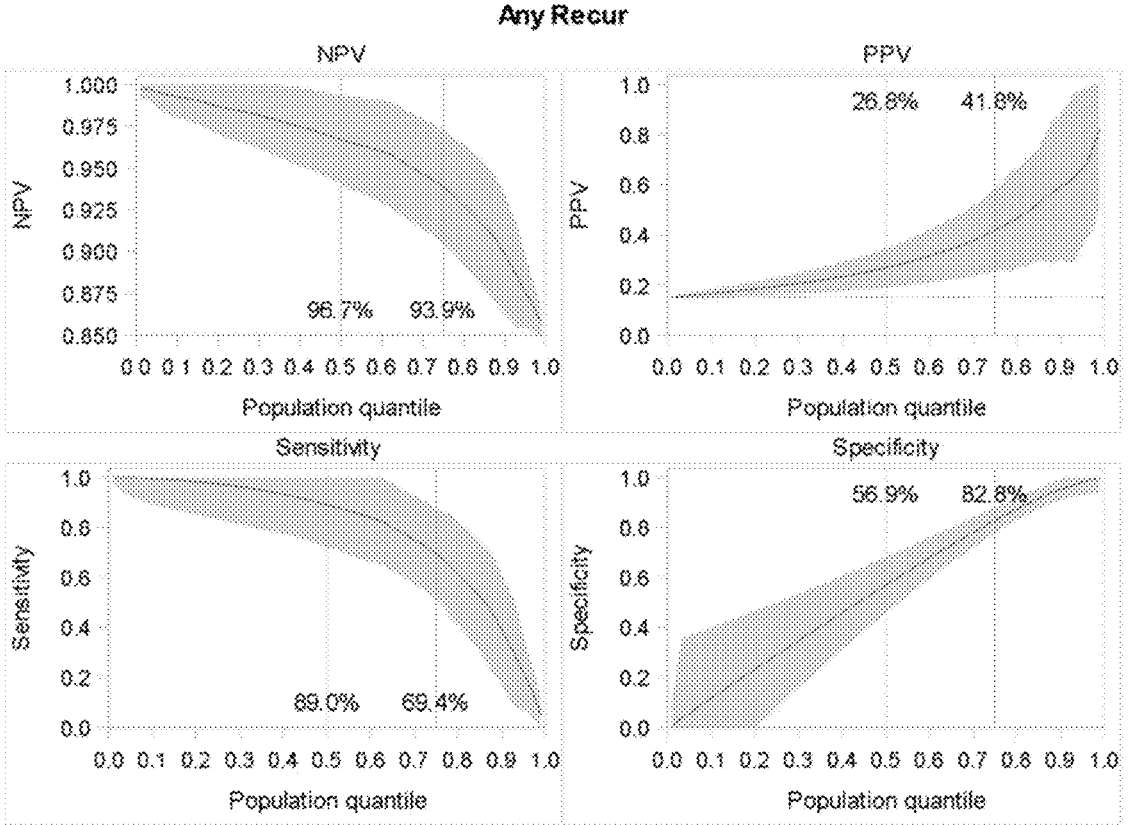
FIG. 8 provides further data of a performance summary for the M1 plus mutation analysis of the concentration of methylated DNA for initial low risk of recurrence patients, as described in Example 3 below. Specifically, FIG. 8 provides negative predictive value (NPV), positive predictive value (PPV), sensitivity, and specificity data for predicting those low risk patients who actually have signs of recurrence.
Figure 9:
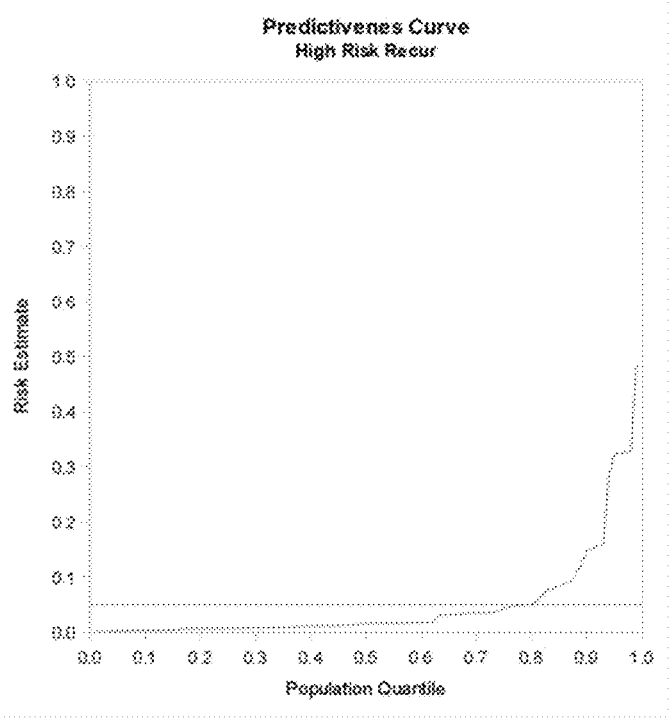
Figure 9:
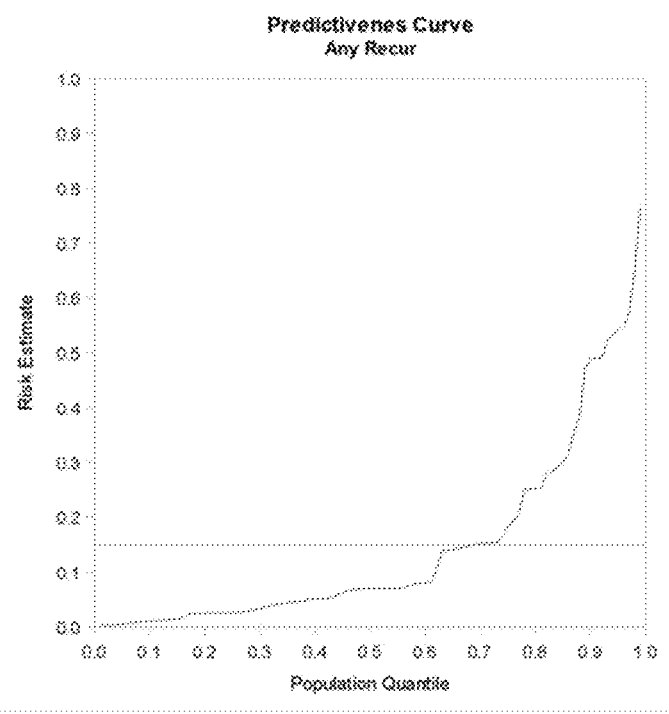
Figure 9:
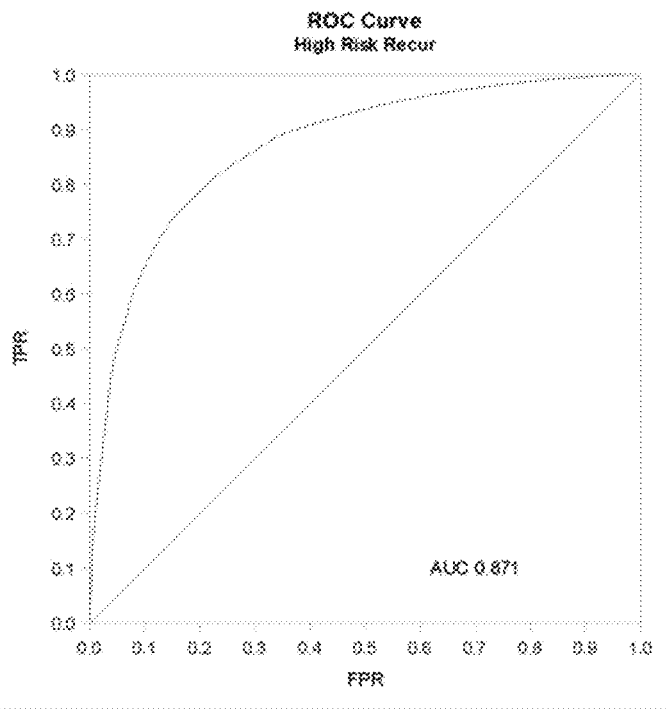
Figure 9:
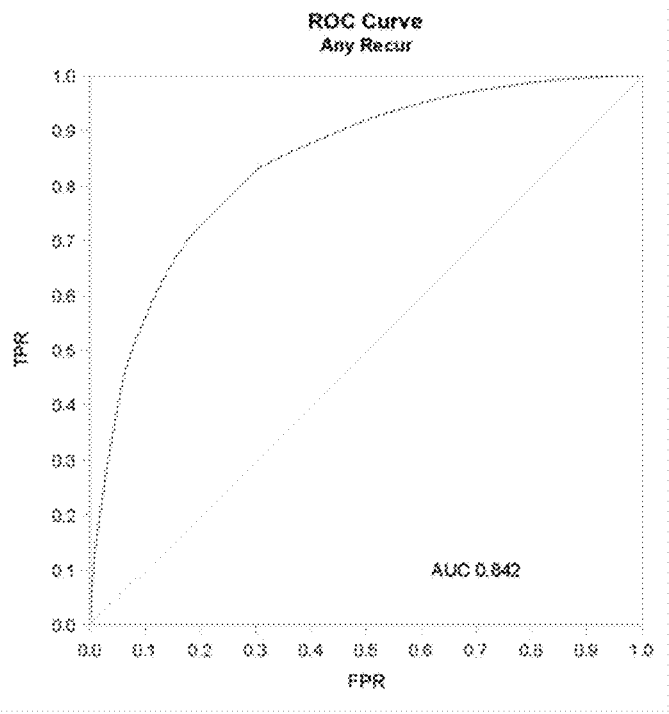

FIG. 9 provides additional data of a performance summary for the M1 plus mutation analysis of the concentration of methylated DNA for initial low risk of recurrence patients, as described in Example 3 below. Specifically, FIG. 9 provides predictiveness curves and ROC curves based on the data in FIGS. 7 and 8.

Figure 10:
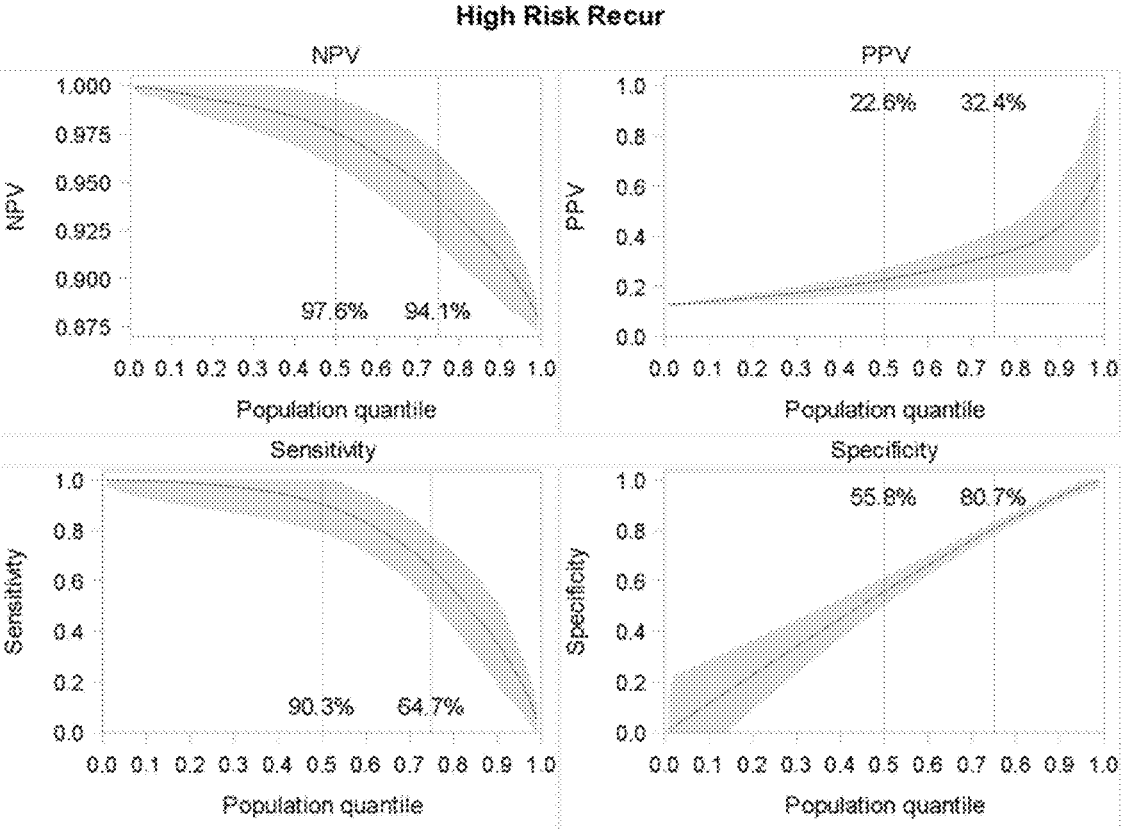

FIG. 10 provides a performance summary for the M1 plus mutation analysis of the concentration of methylated DNA for initial high risk of recurrence patients, as described in Example 3 below. Specifically, FIG. 10 provides negative predictive value (NPV), positive predictive value (PPV), sensitivity, and specificity data for predicting those high risk patients who are actually at high risk of recurrence.

Figure 11:
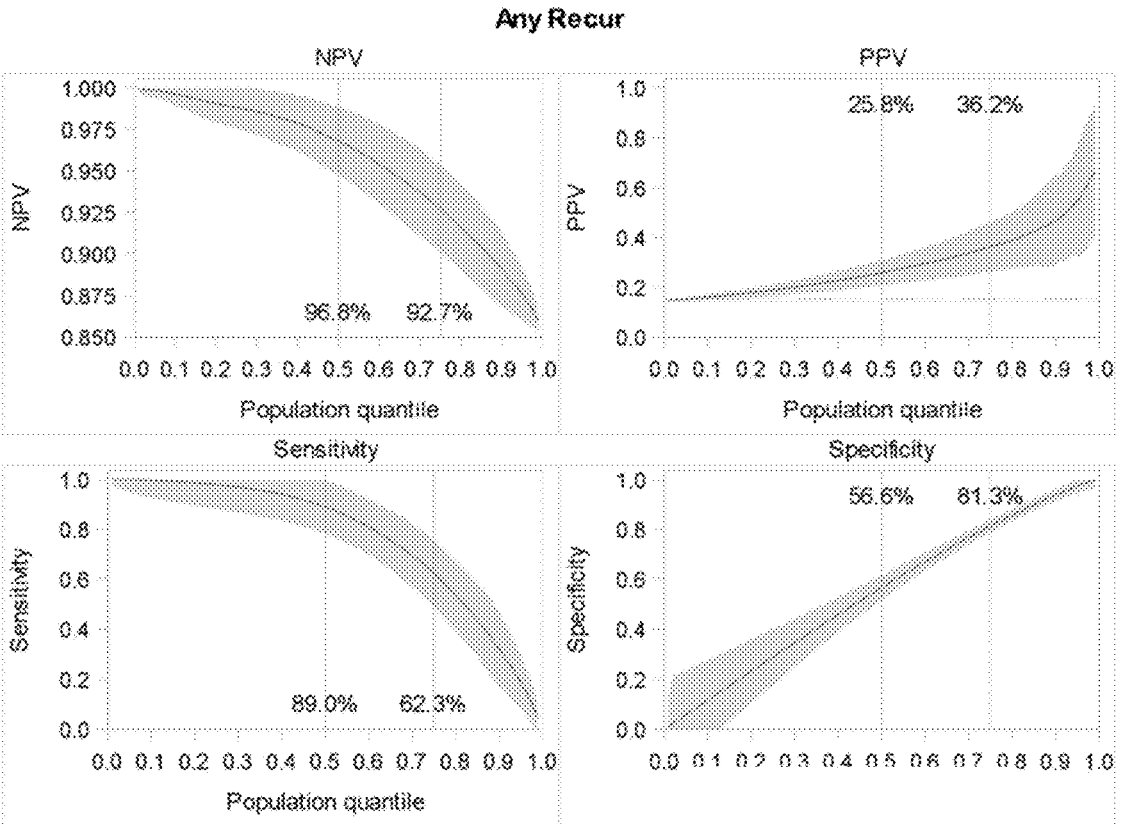

FIG. 11 provides further data of a performance summary for the M1 plus mutation analysis of the concentration of methylated DNA for initial high risk of recurrence patients, as described in Example 3 below. Specifically, FIG. 11 provides negative predictive value (NPV), positive predictive value (PPV), sensitivity, and specificity data for predicting those high-risk patients who actually have signs of recurrence.

Figure 12:
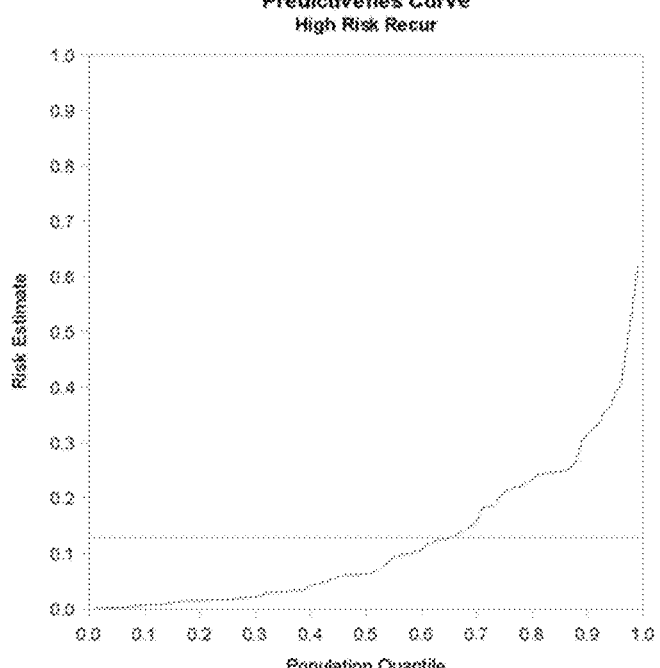
Figure 12:
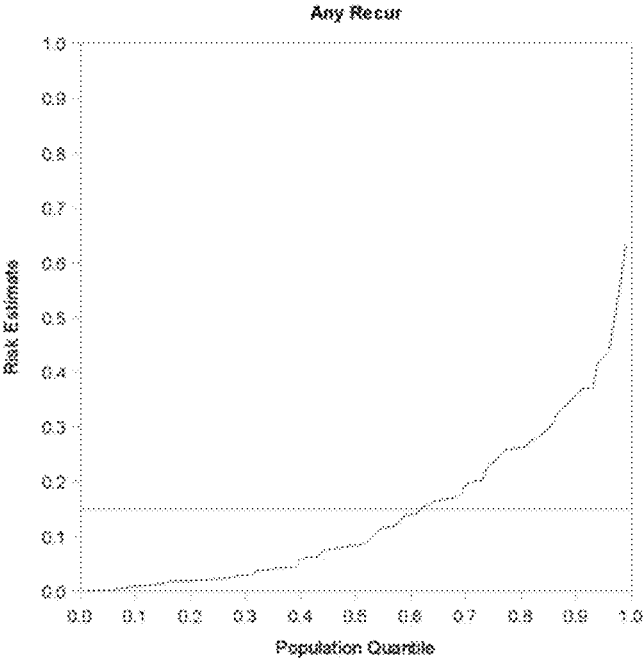
Figure 12:
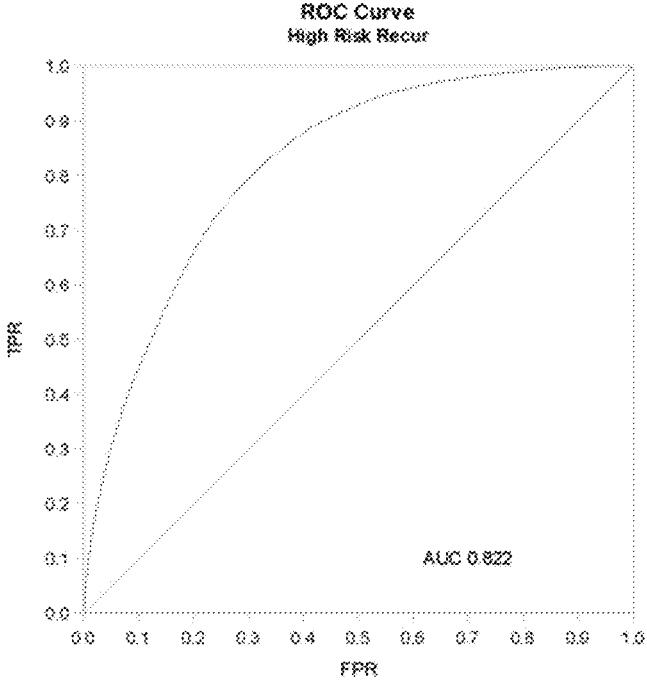
Figure 12:
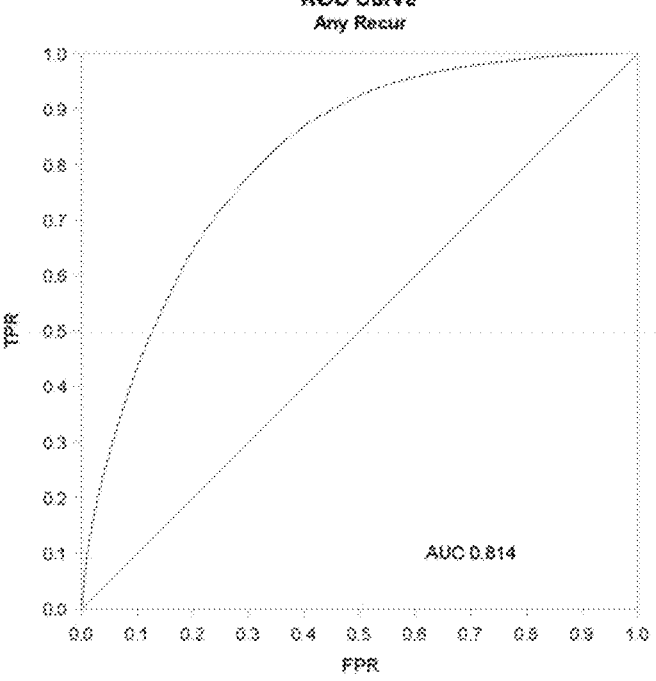

FIG. 12 provides additional data of a performance summary for the M1 plus mutation analysis of the concentration of methylated DNA for initial high risk of recurrence patients, as described in Example 3 below. Specifically, FIG. 12 provides predictiveness curves and ROC curves based on the data in FIGS. 10 and 11.

Figure 13:
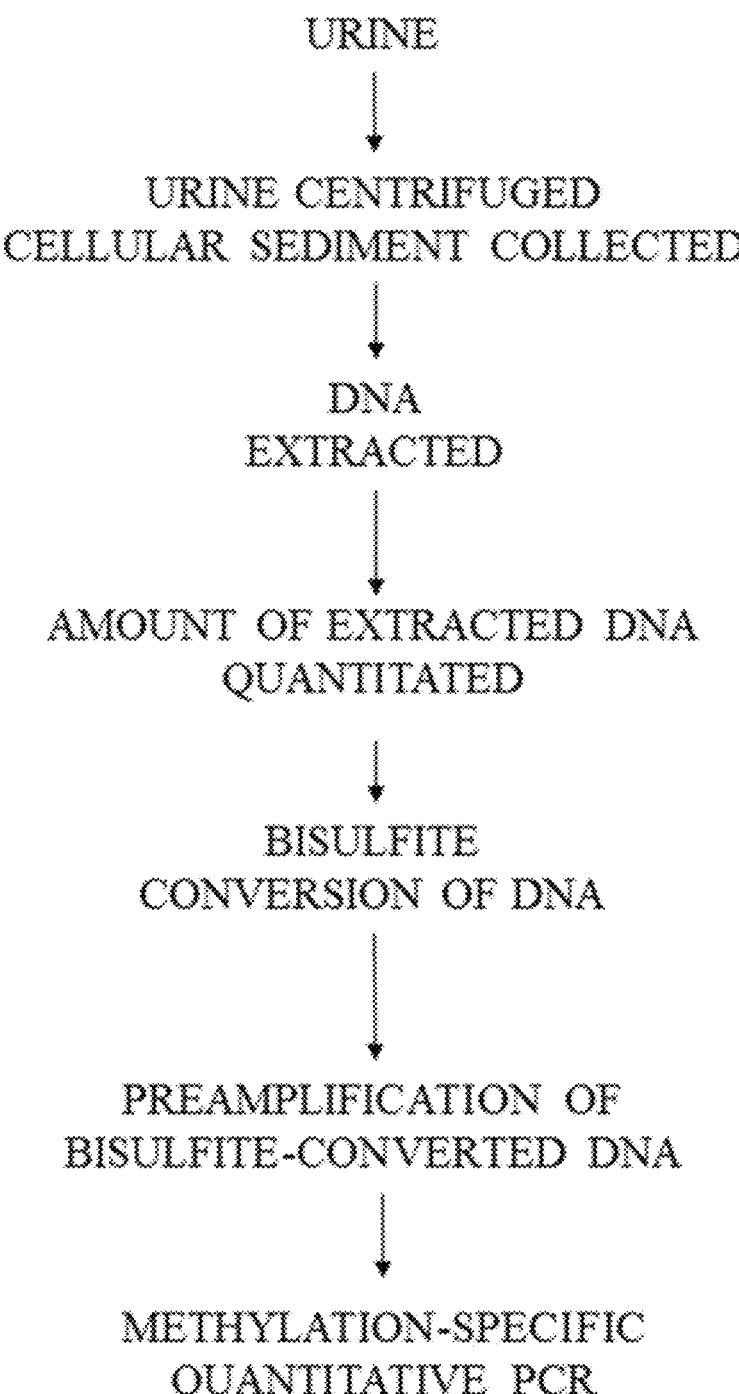

FIG. 13 shows a flow chart of steps in a methylation assay process as disclosed herein.

DETAILED DESCRIPTION

Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, NY 1994), and March, Advanced Organic Chemistry Reactions, Mechanisms and Structure 4th ed., John Wiley & Sons (New York, NY 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described herein. For purposes of the invention, the following terms are defined below.

The terms "tumor" and "lesion" as used herein, refer to all neoplastic cell growth and proliferation, whether malignant or benign, and all pre-cancerous and cancerous cells and tissues. Those skilled in the art will realize that a tumor tissue sample may comprise multiple biological elements, such as one or more cancer cells, partial or fragmented cells, tumors in various stages, surrounding histologically normal-appearing tissue, and/or macro or micro-dissected tissue.

The terms "cancer," "cancerous," and "carcinoma" refer to or describe the physiological condition in mammals that is typically characterized by unregulated cell growth. As used herein, the term "bladder cancer" refers to cancer that has arisen from the bladder. Examples of bladder cancer include, for example, "non-muscle invasive bladder cancer" or "NMIBC" and "muscle invasive bladder cancer" or "MIBC."

The America Joint Committee on Cancer (AJCC) TNM staging system (7th ed., 2010) may be used to stage bladder cancer. The TNM staging system considers (T) how far the main or primary tumor has grown through the bladder wall and whether it has grown into nearby tissues, (N) whether the cancer has spread to lymph nodes near the bladder, and (M) whether or not the cancer has metastasized to distant sites such as other organs or lymph nodes not near the bladder. The TNM staging system for bladder cancer is as follows:

Primary Tumor (T)

Tx Primary tumor cannot be assessed

T0 No evidence of primary tumor

Ta Non-invasive papillary carcinoma

Tis Non-invasive flat carcinoma (flat carcinoma in situ, or CIS)

T1 Tumor has grown from the layer of cells lining the bladder into the connective tissue below, but has not grown into the muscle layer of the bladder T2 Tumor has grown into the muscle layer T3 Tumor has growth through the muscle layer into the fatty tissue surrounding it T4 Tumor has spread beyond the fatty tissue into nearby organs or structures including any of: prostate stroma, seminal vesicles, uterus, vagina, pelvic wall, or abdominal wall Regional Lymph Nodes (N)

NX Regional lymph nodes cannot be assessed

N0 No regional lymph node metastasis

N1 Cancer has spread to a single regional lymph node in the true pelvis

N2 Cancer has spread to two or more lymph nodes in the true pelvis

N3 Cancer has spread to lymph nodes along the common iliac artery

Distant Metastasis (M)

M0 No distant metastasis

M1 Distant metastasis has occurred

Bladder Cancer Stages

| Stage 0a | Ta | N0 | M0 | |
|---|---|---|---|---|
| Stage 0is | Tis | N0 | M0 | |
| Stage 1 | T1 | N0 | M0 | |
| Stage II | T2 | N0 | M0 | |
| Stage III | T3 or T4 | N0 | M0 | (if T4, the cancer may have spread to prostate, uterus, or vagina but not through the abdominal wall) |
| Stage IV | T4 | Any N | M0 | (in which the T4 cancer has spread through the abdominal wall) |
| | Any T | N1 to N3 | M0 | |
| | Any T | Any N | M1 | |

Reference to tumor "stage," as used herein, refers to how far the tumor(s) has spread, and refers to any of the Stages I, II, III, or IV above for bladder cancer, which are based on the T, N, and M criteria given above.

Reference to tumor "grade," as used herein, refers to the grading of bladder cancer, based on how the cancer cells look under a microscope. "Low grade" (also called "well-differentiated") cancers look more like normal tissue under a microscope. "High grade" (also called "poorly differentiated" or "undifferentiated") cancers look less like normal tissue under a microscope. Low grade cancers tend to have a better prognosis than high grade cancers.

The term "prognosis" is used herein to refer to the prediction of the likelihood that a cancer patient will have a cancer-attributable death or progression, including recurrence, metastatic spread, and drug resistance, of a neoplastic disease, such as bladder cancer.

The term "prediction" or "predict" is used herein to refer to the likelihood that a cancer patient will have a particular response to treatment, whether positive (aka. a "beneficial response") or negative, following surgical removal of the primary tumor. For example, treatment could include targeted drugs, immunotherapy, or chemotherapy.

Unless indicated otherwise, each gene name used herein corresponds to the Official Symbol assigned to the gene and provided by Entrez Gene (URL: www (dot) ncbi (dot) nlm (dot) nih (dot) gov (slash) sites (slash) entrez) as of the filing date of this application.

The terms "correlated" and "associated" are used interchangeably herein to refer to the association between two different measurements or between a measurement or series of measurements, such as an amount or concentration of methylation in a sample or presence of a mutation, and an event, such as recurrence.

The terms "recurrence" and "relapse" are used herein, in the context of potential clinical outcomes of bladder cancer, refer to recurrence of either local or distant metastases. Identification of a recurrence could be done by, for example, one or more of cystoscopy, cytology, CT imaging, ultrasound, arteriogram, or X-ray, biopsy, urine or blood test, physical exam, or research center tumor registry.

As used herein, "cystoscopy" refers to a procedure in which a cystoscope instrument is inserted into the urethra to allow visualization of the urethra and urinary bladder, and optionally, to remove tissue samples for further analysis.

As used herein, a "transurethral resection" or "transurethral resection of bladder tumor" (TUR or TURBT) refers to a procedure in which a doctor removes suspected tumor tissue and optionally surrounding tumor muscle tissue, for example, to determine if the tumor is indeed cancerous and if it has invaded surrounding muscle tissue. TURBT and subsequent analysis can be used, for example, to determine stage and grade of a tumor.

As used herein, "cytology" refers to a process of examining bladder tissue or washings from cytology or TURBT, or of examining a urine sample under a microscope to look for the presence of potential bladder cancer cells and/or to assess the morphology of the cells to determine the grade of the cells.

The terms "surgery" or "surgical resection" are used herein to refer to surgical removal of some or all of a tumor, and usually some of the surrounding tissue. Examples of surgical techniques include TURBT, laparoscopic procedures, biopsy, or tumor ablation, such as cryotherapy, radio frequency ablation, and high intensity ultrasound. In cancer patients, the extent of tissue removed during surgery depends on the state of the tumor as observed by a surgeon.

The term "active surveillance," when applied to a bladder cancer patient, refers to the process of monitoring such a patient after primary treatment for bladder cancer, for example, to check for recurrence events, or to determine the risk of a future recurrence in the patient. A "surveillance visit," for example of a patient to an oncologist or other doctor, refers to a visit intended as part of the patient's surveillance procedure, such as a visit in which a urine test, cystoscopy procedure, or the like is performed. A patient under active surveillance may have, for example, 1, 2, 3, or 4 surveillance visits per year depending on the patient's recurrence risk and the stage or grade of the cancer. Cystoscopy may be performed at one or more of such annual visits.

The term "Cp" as used herein refers to "crossing point." The Cp value is calculated by determining the second derivatives of entire qPCR amplification curves and their maximum value. The Cp value represents the cycle at which the increase of fluorescence is highest and where the logarithmic phase of a PCR amplification process begins.

The term "methylation fraction" or "MF" refers to an estimation of the percentage or fraction of a particular gene or set of genes that has been methylated. Methylation may be estimated from a methylation-specific Cp according to mathematical formulas described herein.

The term "amount of methylated DNA" in a sample refers to the MF multiplied by the sample DNA yield, and may be measured in gram-based units such as nanograms. The amount of methylated DNA may be determined for each gene and then averaged to obtain a "mean amount of methylated DNA" for the sample. The term "concentration of methylated DNA" in a sample refers to the MF multiplied by the sample DNA yield over the sample volume. The concentration of methylated DNA may be determined in nanograms per mL units, for example, and it may be determined for each gene and then averaged to obtain a "mean concentration of methylated DNA" for the sample.

A "reference set of bladder cancer patients," for example, may be used to estimate how a particular patient's methylation and optionally mutation data compares to data from bladder cancer patients as a whole. Thus, a reference set may include patients known to have both low and high risks of recurrence or who were known to have had a recurrence or not to have recurred. Data from a reference set may therefore provide a range of possible recurrence risks correlated with amount or concentration of methylated DNA, for example, against which new data for an individual patient may be compared.

The term "Hazard Ratio (HR)" as used herein refers to the effect of an explanatory variable on the hazard or risk of an event (i.e. recurrence or death). In proportional hazards regression models, the HR is the ratio of the predicted hazard for two groups (e.g. patients with two different stages of cancer) or for a unit change in a continuous variable (e.g. one standard deviation change).

The term "negative predictive value" or "NPV" is the probability that a subject with a negative result in a diagnostic assay actually does not have the condition or risk for which the subject is being tested. It may be expressed as the number of true negative subjects divided by the sum of the true negative and the false negative, expressed as a percentage.

The term "positive predictive value" or "PPV" is the probability that a subject with a positive result in a diagnostic assay actually does have the condition or risk for which the subject is being tested. It may be expressed as the number of true positive subjects divided by the sum of the true positive and the false positive, expressed as a percentage.

The term "sensitivity" refers to the ability of a diagnostic test to correctly identify those having the condition that the test is intended to diagnose (i.e. the true positive rate). Thus, if a test is highly sensitive, for example, a patient with a negative result can be more confident that the negative result is accurate.

The term "specificity" refers to the ability of a diagnostic test to correctly rule out subjects who do not have the condition being tested (i.e. the true negative rate). Thus, a highly specific test may have a low rate of false positive results.

The term "polynucleotide," when used in singular or plural generally refers to any polyribonucleotide or polyde-oxyribonucleotide, which may be unmodified RNA or DNA or modified RNA or DNA. Thus, for instance, polynucle-otides are defined herein to include, without limitation, single- and double-stranded RNA, and RNA including single- and double-stranded regions, hybrid molecules com-prising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucle-otide" specifically includes cDNAs. The term includes DNAs (including cDNAs) and RNAs that contain one or more modified bases. Thus, DNAs or RNAs with backbones modified for stability or for other reasons, are "polynucle-otides" as that term is intended herein. Moreover, DNAs or RNAs comprising unusual bases, such as inosine, or modi-fied bases, such as tritiated bases, are included within the term "polynucleotides" as defined herein. In general, the term "polynucleotide" embraces all chemically, enzymati-cally and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA/DNA hybrids and double-stranded DNAs. Oligonucleotides, such as single-stranded DNA probe oligonucleotides, are often synthesized by chemical methods, for example using automated oligonucleotide syn-thesizers that are commercially available. However, oligo-nucleotides can be made by a variety of other methods, including in vitro recombinant DNA-mediated techniques and by expression of DNAs in cells and organisms.

Methods of Monitoring Bladder Cancer Patients

The present disclosure includes methods of monitoring bladder cancer patients involving determining the DNA methylation status of the patient and optionally further determining the presence of particular gene mutations preva-lent in bladder cancer. The methods may be performed, for example, to determine a patient's relative risk of recurrence as compared to that of bladder cancer patients as a whole. For example, patients may be undergoing active surveillance following surgical treatment for cancer.

In some embodiments, the methods comprise obtaining a urine sediment sample from the patient, extracting DNA from the sample and exposing the extracted DNA to bisulfite to detect the presence of methylation in particular genes. For example, in some embodiments, the methylation status of at least four genes selected from MEIS1, NKPD1, ONECUT2, KLF2, OSR1, SOX1, EOMES, DDX25, and TMEM106A and from at least one reference gene is determined. In some embodiments, presence or absence of specific mutations in one or both of FGFR3 and TERT genes is also determined. In some embodiments, the FGFR3 mutation is a C to G substitution at chromosome position ch4:1803568 (Acces-sion No. NM_001163213.1), resulting in an amino acid change of S to C at position 249 of the protein. In some embodiments the TERT mutation is a G to A substitution (or a C to T substitution on the opposing strand) at chromosome position chr5:1295228 (Accession No. NM_001193376.1), which results in a mutation in a promoter region for the TERT gene.

In some embodiments, the genes for methylation analysis comprise at least two of, at least three of, or each of MEIS1, NKPD1, ONECUT2, and KLF2. In some embodiments, one or more of the following genes is also used for methylation analysis: EPHX3, IRX5, NID2, VIM, and ITPKB. In some embodiments, one, two, three, or four or more reference genes are assessed in the methylation analysis, for example, for normalizing and thus correcting the signal from the test genes to account for the amount of DNA in the sample. In some embodiments, the reference genes include CTNS, TOP3A, COL2A and SLC24A3.

In some embodiments, the genes for methylation analysis comprise the genes of the M1 model described in Example 3 herein. In some embodiments, the genes for methylation analysis comprise the genes of the M2 model described in Example 3 herein. In some embodiments, the genes for methylation analysis comprise the genes of the M3 model described in Example 3 herein. In some embodiments, the genes for methylation analysis comprise the genes of the M4 model described in Example 3 herein. In some embodi-ments, the genes for methylation analysis comprise the genes of the M5 model described in Example 3 herein. In some embodiments, the genes for methylation analysis comprise the genes of the M6 model described in Example 3 herein. In some embodiments, the genes for methylation analysis comprise the genes of the M7 model described in Example 3 herein. In some embodiments, the genes for methylation analysis comprise the genes of the M8 model described in Example 3 herein. In some embodiments, the genes for methylation analysis comprise the genes of the M9 model described in Example 3 herein.

In some embodiments, the methods herein are used alone or in combination with other diagnostic tests or assays to determine the relative recurrence risk for a patient compared to data from a group of bladder cancer patients of various recurrence risks or actual levels of recurrence. For example, a distribution of recurrence risks can be obtained by noting the outcome of the methylation and optional mutational assay on samples from patients with previously determined recurrence risks from other diagnostic tests or from archived samples from patients who are known to recur or not to recur. For example, such data can be used to create a distribution of test results against recurrence risk for bladder cancer patients. Then, data from a new patient can be compared to data from the distribution to determine if the patient's risk of recurrence is, for example, low or high as compared to the overall average from the distribution, or to determine where the new patient falls along the distribution curve. Such analysis can provide a relative risk of recurrence for the new patient.

In some embodiments, the patient has already been diag-nosed with non-muscle-invasive bladder cancer. In some embodiments, the patient's tumor has previously been diag-nosed as Ta, Tis, T0, or low grade. In some other embodi-ments, the patient's tumor has previously been diagnosed as T1 or high grade. And in some embodiments, the patient has been diagnosed with muscle-invasive bladder cancer. In some embodiments, the patient has been determined to have a low risk of recurrence on the basis of other diagnostic and/or clinical test results. In some embodiments the method is conducted during an active surveillance visit, such as a visit prior to cystoscopy or a visit for the purpose of determining whether cystoscopy should be performed, or a visit for the purpose of determining how frequently cystoscopy should be performed. For example, if the assay herein reveals or confirms that the patient should have a low risk of bladder cancer recurrence, cystoscopy may not be performed directly after the assay is run, or the frequency of cystoscopy may be reduced. If the assay herein reveals that a patient may have a higher risk of recurrence than previously thought, cystoscopy may be performed as part of the active surveillance visit or may be performed in a follow-up visit. In some embodiments, the methods herein may be conducted after a negative cystoscopy, for example, to help confirm a low risk of recurrence. In some embodiments, methods herein are conducted at least once per year, such as once per six months, or once per three months.

In some embodiments, a patient has previously been determined to have a low risk of recurrence based on a Ta or low grade tumor sample comprising tissue from TURBT, cystoscopy, or from an upper GU workup. In some embodiments, the low risk patient has either normal or abnormal cystoscopy. In some embodiments, the low risk patient has either normal or abnormal cytology. In some embodiments, the patient has NMIBC and has a negative tissue analysis result from one or more of TURBT, cystoscopy, or upper GU workup and the methods herein are used to confirm non-recurrence of bladder cancer. In some embodiments, the patient has NMIBC and has previously had a tissue analysis result giving Ta or low grade cancer from one or more of TURBT, cystoscopy, or upper GU workup and the methods herein are used to confirm that the patient has a low risk of bladder cancer recurrence. In such methods, if the methods herein indicate that the patient actually has a high risk of recurrence or indicate any actual presence of recurrence, the frequency of cystoscopy for the patient may be increased in future surveillance visits or further tissue analysis may be performed. For example, in some embodiments, a patient has previously been determined to have a high risk of recurrence based on a high grade, T1-T2, or Tis tumor sample comprising tissue from TURBT, cystoscopy, or from an upper GU workup. In some embodiments, the high risk patient has either normal or abnormal cystoscopy. In some embodiments, the high risk patient has either normal or abnormal cytology. In some embodiments, the patient has NMIBC and has previously had a tissue analysis result from one or more of TURBT, cystoscopy, or upper GU workup showing high grade, T1, T2, or Tis and the methods herein are used to confirm that the patient is at high risk for recurrence and to check for presence of any recurrence. If the methods indicate that the patient is actually at low risk of recurrence, the frequency of cystoscopy may be reduced. If the methods indicate that the patient is experiencing an actual recurrence, then further tissue analysis may be performed.

In some embodiments, an abnormal cystoscopy result comprises any abnormality requiring a follow-up TURBT, upper GU tract workup or follow-up cystoscopy. In some embodiments, an abnormal cytology result comprises any abnormality leading to TURBT or upper GU tract workup or follow-up cystoscopy.

In some embodiments, the diagnostic methods herein may be included as part of a method of treatment, for example, for a patient otherwise determined to have a low risk of recurrence. For example, if the patient is confirmed to have a low risk of recurrence according to the methods herein, the patient may continue to be treated by active surveillance. In some embodiments, the frequency of cystoscopy may be reduced. In other embodiments, if the patient is determined to have a higher risk of recurrence according to the methods herein, the frequency of cystoscopy may be increased.

Methods of Assaying Gene Methylation and Mutation

Gene methylation in bladder cancer patients may be assayed from a sample from the patient, such as a urine sample. After collection of a urine sample, the sample may be treated, for example by centrifugation, to isolate cellular sediment from the urine sample. DNA may then be extracted from the sediment, for example, using a DNA isolation kit such as a Qiagen AllPrep DNA/RNA MiniKit® or other type of commercially available DNA extraction kit.

After extraction of DNA, the total amount of DNA in the sample may be quantitated, for example in nanograms, and then subjected to bisulfite conversion for methylation analysis. For example, cytosine nucleotides in CpG dinucleotide repeats are a key target site for methylation, in which cytosine is converted to 5-methyl-cytosine. Addition of sodium bisulfite to the DNA converts unmethylated cytosines to uracils while leaving methylated cytosines unmodified. Thus, the presence of methylated cytosines may be detected upon amplifying a bisulfate-treated DNA strand, for example with appropriate primers with modified sequences to accommodate the expected uracil conversions. Methylated cytosines still read as cytosines when sequenced while unmethylated cytosines read as uracils. See, e.g., K. Patterson et al., *J. Vis. Exp.* 56: e3170 doi: 10.3791/3170 (2011); R. Shapiro et al., *J. Am. Chem. Soc.* 92(3): 422-424 (1970); H. Hayatsu et al., *J. Am. Chem. Soc.* 92(3): 724-6 (1970); and M. Frommer, *Proc. Natl. Acad. Sci.*, USA 89(5); 1827-31 (1992), for descriptions of bisulfite conversion of methylated DNA. Commercial kits such as EpiTect® Fast DNA Bisulfite Kit (Qiagen; EpiBeat) may be used to perform bisulfite conversion.

Following bisulfite conversion and prior to detection of methylated DNA, the targeted genes of the DNA may be pre-amplified using a polymerase capable of amplifying GC-rich DNA regions. An example is KAPA Taq Hotstart Polymerase™ (KAPA Biosystems). Preamplification may be performed, for example, using KAPA Probe Fast™ qPCR kits (KAPA Biosystems). Following preamplification, further PCR amplification, such as by methylation specific quantitative PCR (MS-qPCR) may then be performed, again using polymerases capable of amplifying GC-rich regions, such as with a KAPA Probe Fast™ kit.

In PCR analysis, 5'-nuclease assay data are commonly initially expressed as a threshold cycle ("$C_T$"). Fluorescence values are recorded during every cycle and represent the amount of product amplified to that point in the amplification reaction. The threshold cycle ($C_T$) is generally described as the point when the fluorescent signal is first recorded as statistically significant. Data may also be expressed as a crossing point ("Cp"). The Cp value is calculated by determining the second derivatives of entire qPCR amplification curves and their maximum value. The Cp value represents the cycle at which the increase of fluorescence is highest and where the logarithmic phase of a PCR amplification begins.

In some embodiments, qPCR may also be used to detect mutations in particular genes or gene regulatory regions. PCR detection of mutations may in some embodiments be performed in the same PCR reaction as detection of gene methylation, for example, by including primers to the genes of interest modified to account for bisulfite treatment. For example, in some embodiments, mutations in genes such as FGFR3 and TERT may also be detected. For example, in some embodiments, the FGFR3 mutation found at genomic position (HG19) chr4: 1803568 is detected. That mutation involves a change of a C to a G in the DNA sequence, resulting in an S249C amino acid change in the protein. In some embodiments, the TERT mutation found at genomic position (HG19) chr5: 1295228 is detected. That mutation involves a change of a G to an A in the DNA sequence of a promoter region for the gene.

To minimize errors and the effect of sample-to-sample variation, PCR can be performed using an internal standard. The ideal internal standard gene (also referred to as a reference gene) either does not contain any CpG dinucleotides and so is not methylated to any higher or lower degree in a bladder cancer patient than in a non-bladder cancer patient, or for other reasons is unchanged in methylation in a cancer patient. Thus, qPCR data on a reference gene should be reflective of the amount of DNA in the sample rather than the degree of DNA methylation.

Design of PCR Primers and Probes

More generally, PCR primers and probes for genes of interest can be designed, for example, based upon exon or intron sequences present in the mRNA transcript of the gene of interest or based on promoter regions on either side of a gene of interest, and based on expected sequence modifications due to bisulfite conversion. Primer/probe design can be performed using publicly available software, such as the DNA BLAT software developed by Kent, W. J., *Genome Res.* 12(4):656-64 (2002), or by the BLAST software including its variations.

Where necessary or desired, repetitive sequences of the target sequence can be masked to mitigate non-specific signals. Exemplary tools to accomplish this include the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. (See S. Rrawetz, S. Misener, *Bioinformatics Methods and Protocols: Methods in Molecular Biology*, pp. 365-386 (Humana Press).)

Other factors that can influence PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases, and exhibit Tm's between 5° and 80° C., e.g. about 50 to 70° C. In some embodiments, PCR primers or blocking nucleic acids may comprise DNA or may comprise DNA analogs such as locked nucleic acids (LNA) or protein nucleic acids (PNA).

For further guidelines for PCR primer and probe design see, e.g. Dieffenbach, C W. et al, "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

Algorithms and Statistical Analysis Methods

The methylation fraction of the genes to be analyzed, in some embodiments, is determined using real-time or quantitative PCR technology. For example, a crossing point or Cp value may represent the PCR cycle at which, for instance, methylation of a particular gene is first detected in a patient's sample. This information can be compared to a previously obtained standard curve of Cp value versus log 10 concentration for the methylated gene and then normalized to a similar value for a reference gene, in order to obtain a methylation fraction for that gene. This is illustrated in the equations below, in which m represents data from the test gene and a represents data from a methylation-independent (MIP) reference gene:

$$m = \frac{C_p(\text{gene}) - \text{intercept (gene)}}{\text{slope (gene)}} \quad \alpha = \frac{C_p(MIP) - MIPintercept}{MIPslope}$$

$$\text{Methylation Fraction} = 2^{m-\alpha}$$

First, a standard curve plotting, for example, Cp against log 10 gene concentration may be determined for each gene by taking a DNA sample of known concentration representing a PCR amplification product for the methylated or unmethylated version of the gene and performing a set of serial dilutions and measuring the fluorescence signal at each concentration and relating that fluorescence signal to a PCR cycle value corresponding to that signal. Such a Cp versus log 10 concentration curve may be linear over several orders of magnitude, allowing a slope and intercept to be determined (see the equations above). (See, e.g., D. Rodriguez-Lazaro & M. Hernandez, Introduction to the Real-Time PCR, in *Real-Time PCR in Food Science: Current Technology and Applications*, D. Rodriguez-Lazaro Ed., Caister Academic Press, Norfolk, UK (2013) for description of how to obtain and utilize such a standard curve.)

For example, a 15-point linearity analysis to obtain such a slope and intercept may be performed by taking a nucleic acid of known concentration and performing 14 two-fold serial dilutions and also obtaining a $15^{th}$ sample comprising no nucleic acid. Expression of the associated gene in each of the 15 samples is then determined by conducting PCR on each sample and determining Cp value, with the Cp value for the no nucleic acid sample expected to equal the number of PCR cycles (e.g. 40). If the PCR reaction is perfect, then there should be an increase of Cp value by 1 for each two-fold dilution. The observed Cp values are plotted against the known starting concentration of the nucleic acid and the slope of the resulting line and its intercept are calculated.

Once the slope and intercept for this standard curve (and a similar standard curve for one or more reference genes) have been obtained, they may be used to calculate m and α values and subsequently, the methylation fraction (MF) for the test gene (see equations above). To ensure that the MF value falls between zero and one, the MF in some embodiments may be equal to the maximum of (a) zero or (b) the value corresponding to the minimum of 1 or $2^{m-\alpha}$. This may be expressed as: $MF=\max(0, \min(1, 2^{m-\alpha}))$.

The MF for each gene of interest may then be used to calculate other values. In some embodiments, an amount of methylated DNA, equal to the MF multiplied by the DNA yield of the sample (for example, in nanograms) is also determined for each gene. In some embodiments, the amount of methylated DNA may reflect how much tumor-related DNA is actually "leaking" into a patient's urine. And in other embodiments, the concentration of methylated DNA is determined, which is equal to the amount of methylated DNA divided by the sample volume (for example, in milliliters). The concentration of methylated DNA may correct for the concentration of tumor-related DNA in the sample that a test laboratory receives, for example, and so may not be affected in case only a portion of a urine sample is received by the laboratory. However, this value may be affected by the amount of liquid the patient consumes prior to urine collection. In some embodiments, both the amount and the concentration of methylated DNA may be determined for a gene.

In some embodiments, a mean amount or concentration of methylated DNA is then determined for a set of genes being assayed. For example, in some embodiments, at least four, at least five, or at least six test genes are assayed. In such cases, a mean amount or mean concentration of methylated DNA may be reported in an algorithm herein. In some embodiments, the amount and/or concentration of methylated DNA may be calculated for each gene of a set of genes and then the values averaged.

In some embodiments, gene mutations are also assessed. In some embodiments, such mutations may also be assessed using real-time or quantitative PCR methods. Thus, for example, a mutation may be considered to be present if a fluorescence signal associated with an amplification product for that mutation is detected by a particular crossing point in a PCR amplification. In some embodiments, for example, mutations in FGFR3 and/or TERT are also included in the assays herein. In some embodiments, the FGFR3 mutation is at chromosome position chr 4:1803568, which changes a C to a G, resulting in an S249C mutation in the protein. In some embodiments, the TERT mutation is at chromosome position chr5:1295228, which changes a G to an A, resulting in a mutation in a promoter region.

In some embodiments, an algorithm may be developed from the mean amount or concentration of methylated DNA from the test genes and optionally also from the presence or absence of the FGFR3 and/or TERT mutations. In some embodiments, the algorithm may involve the following set of steps:

1) For each methylation marker gene and reference gene, correct for differential PCR amplification efficiency using the intercept and slope estimated from an associated standard curve, as discussed above.

2) Calculate the m and $\alpha$ values of the marker and reference genes, where an average $\alpha$ value is used in the methylation fraction equation when more than one reference gene is included in the analysis 3) Estimate Methylation Fraction for each gene as MF=max (0, (min 1, $2^{m-\alpha}$)

4) Apply selected method (a) or (b) to quantify methylation of individual genes:
   a. Amount of methylated DNA amount=MF*Sample yield (ng), or
   b. Concentration of methylated DNA conc=MF*Sample yield (ng)/Sample Volume (mL)

5) Calculate Log 10 (average amount or conc across the genes)

6) Optionally, also define presence of mutations in FGFR3 and TERT

In some embodiments, a threshold Cp value for presence of each mutation is defined as the number of cycles by which fluorescence signal associated with the mutation must appear for a mutation to be called as being present. To evaluate performance of the final algorithms, in some embodiments, a multinomial logistic regression model with categories of HR recurrence, LR recurrence and no recurrence was fit with the following predictor variables:

2 degrees of freedom natural cubic spline to the method of choice:
   Log 10 (average amount), or
   Log 10 (average conc)
Indicators for FGFR3 and TERT mutations, if included in the assay
Indicator for patient subgroups (i.e., initial low risk of recurrence ("initial LR") or initial high risk of recurrence ("initial HR"))

From these steps, in some embodiments, regression analysis may be used to provide a range of "scores" for bladder cancer patients, thus creating a reference curve of risk of recurrence or actual recurrence against a "score" from the algorithm against which data for a new patient may be compared. Such a curve may then be used to determine a relative risk of recurrence, for example, for that new patient.

In some embodiments, the genes assayed in the above algorithms comprise at least 4 genes selected from MEIS1, NKPD1, ONECUT2, KLF2, OSR1, SOX1, EOMES, DDX25, and TMEM106A and optionally further genes selected from EPHX3, IRX5, NID2, VIM, and ITPKB) and one or more reference genes. In some embodiments, the genes assayed comprise each of MEIS1, NKPD1, ONECUT2, and KLF2. In some embodiments, the genes assayed in the above algorithms comprise or consist of those of the M1 gene set listed in Example 3 below along with one or more reference genes. In some embodiments, the genes assayed in the above algorithms comprise or consist of those of the M2 gene set listed in Example 3 below along with one or more reference genes. In some embodiments, the genes assayed in the above algorithms comprise or consist of those of the M3 gene set listed in Example 3 below along with one or more reference genes. In some embodiments, the genes assayed in the above algorithms comprise or consist of those of the M4 gene set listed in Example 3 below along with one or more reference genes. In some embodiments, the genes assayed in the above algorithms comprise or consist of those of the M5 gene set listed in Example 3 below along with one or more reference genes. In some embodiments, the genes assayed in the above algorithms comprise or consist of those of the M6 gene set listed in Example 3 below along with one or more reference genes. In some embodiments, the genes assayed in the above algorithms comprise or consist of those of the M7 gene set listed in Example 3 below along with one or more reference genes. In some embodiments, the genes assayed in the above algorithms comprise or consist of those of the M8 gene set listed in Example 3 below along with one or more reference genes. In some embodiments, the genes assayed in the above algorithms comprise or consist of those of the M9 gene set listed in Example 3 below along with one or more reference genes. In some embodiments, the reference genes comprise one or more of CTNS, TOP3A, COL2A, and SLC24A3.

In some embodiments, the performance of an algorithm may be monitored, for example, in a test population with known clinical outcomes, by assessing negative predictive value (NPV), sensitivity, positive predictive value (PPV), and specificity. For example, for patients initially diagnosed as having a low risk recurrence (LR), the methods herein may be used to confirm a LR diagnosis. In such a case, the NPV may measure how accurately the methods herein correctly predict a negative result, i.e. that the patient does not have a high risk of recurrence. The sensitivity may reflect, for example, the percentage of truly positive results that are correctly predicted by the test, i.e. that are true positives and not false positives. These measurements, for example, may indicate the accuracy of the test in confirming a recurrence diagnosis. Similarly, in a test used on patients initially diagnosed with a high risk recurrence (HR), the methods may be used to confirm that no recurrences are likely to occur. The PPV and specificity, in some embodiments, may also be determined in order to assess how accurately the test predicts a positive result, and to assess the percentage of truly negative results that are correctly predicted by the test, respectfully. In some embodiments, a goal of the methods is to show a high sensitivity and a high NPV (e.g. greater than 85%, such as greater than 88%, such as greater than 90% sensitivity and greater than 90%, such as greater than 95%, such as greater than 97%, such as greater than 98% NPV) as this might allow for reduction in the frequency of cystoscopy for patients undergoing surveillance.

In some embodiments, further performance evaluations may be conducted, for example determining predictiveness curves, i.e. plots of estimated probability of a high risk of recurrence or any actual recurrence against the population quantile of probability, or determining ROC curves, i.e. plots of the sensitivity versus 1 minus the specificity of a test, which may include cutpoints at each probability of recurrence, or determining area under an ROC curve.

One skilled in the art will recognize that there are otherwise many statistical methods that may be used to determine whether there is a significant relationship between an outcome of interest (e.g., likelihood of survival, likelihood of recurrence) and a particular marker or parameter (e.g., methylation status of a gene or presence or absence of a genetic mutation). This relationship can be presented as a continuous Recurrence Score® (RS), or patients may be stratified into risk groups (e.g., low and high or low, intermediate, and high).

Kits and Systems of the Invention

The materials for use in the methods of the present invention are suited for preparation of kits. The present disclosure thus provides kits comprising agents, which may include gene-specific or gene-selective probes and/or primers, for quantitating the methylation and optionally mutation of the disclosed genes, for example. Kits may also include blocking nucleic acids, for example, to block DNA repeat regions during PCR amplifications. Such kits may optionally contain reagents for the extraction of DNA from samples and for bisulfite conversion of DNA. In addition, the kits may optionally comprise the reagent(s) with an identifying description or label or instructions relating to their use in the methods of the present invention. The kits may comprise containers (including matrices, microtiter plates, and the like suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP), DNA polymerase, and one or more probes and primers of the present invention (e.g., appropriate primers for each test gene and reference gene for methylation analysis as well as for FGFR3 and TERT mutation analysis). Mathematical algorithms used to estimate or quantify prognostic or predictive information are also potential components of kits. Kits may also form part of a system that comprises, for example, detection devices and/or computer software for determining methylation and mutation status of a patient and for comparing patient results against those of a reference bladder cancer patient population.

In some embodiments, kits may comprise forward and reverse primers for PCR amplification of bisulfite modified genes for performing a methylation assay as described herein (e.g. at least 4 genes selected from MEIS1, NKPD1, ONECUT2, KLF2, OSR1, SOX1, EOMES, DDX25, and TMEM106A and optionally further genes selected from EPHX3, IRX5, NID2, VIM, and ITPKB), and for one or more reference genes, and optionally also for evaluating FGFR3 and/or TERT mutation status. Kits may also comprise PCR reagents such as a polymerase capable of amplifying GC-rich sequences, as well as instructions for performance of the assay. Kits may also form part of a system comprising computer software for performing the methylation and optional mutation analysis and for determining a recurrence risk for the patient.

In some embodiments, kits may comprise a cartridge comprising at least one well (which may constitute a channel, chamber, area, or surface). As used herein, a "cartridge" is a generic term meaning a physical structure that can hold reagents and that contains at least one "well." A "well," in turn, is a generic term meaning a channel, chamber, area, or surface that can be used to contain one or more reaction steps such as a step of a PCR process, a DNA extraction from a sample, a wash step, or a detection step, or the like. In some embodiments, at least one well may comprise one or more primers for detecting methylation of genes. The genes may include at least 4 genes selected from MEIS1, NKPD1, ONECUT2, KLF2, OSR1, SOX1, EOMES, DDX25, and TMEM106A and optionally further genes selected from EPHX3, IRX5, NID2, VIM, and ITPKB and optionally also gene mutations, such as in TERT or FGFR3. In some embodiments, methylation is detected for each of the genes MEIS1, NKPD1, ONECUT2, and KLF2. In some embodiments, methylation is detected for the genes of the M1, M2, M3, M4, M5, M6, M7, M8, or M9 gene sets listed in Example 3 below. In some embodiments, the primers are attached to one or more wells in the cartridge. In some embodiments, each well may comprise primers for more than one gene, such as two, three, four, five or six different genes, for example, by using primers labeled with different color labels. In some embodiments, at least one well comprises at least one primer for detecting methylation of at least one reference gene. In some embodiments, the cartridge is configured so that each well comprises primers for detecting methylation in one or more of the above gens MEIS1, NKPD1, ONECUT2, KLF2, OSR1, SOX1, EOMES, DDX25, TMEM106A, EPHX3, IRX5, NID2, VIM, and ITPKB, and further primers for detecting methylation of at least one reference gene. In some embodiments, the reference genes comprise one or more of CTNS, TOP3A, COL2A and SLC24A3. Thus, in some embodiments, the cartridge is configured to perform methylation-specific quantitative PCR on the genes, meaning that it's structure and arrangement is such that it can be used for carrying out a methylation-specific quantitative PCR analysis of the genes.

In some embodiments, the cartridge further comprises amplification reagents such as PCR enzymes, buffers, nucleotide triphosphates (e.g. dATP, dCTP, dGTP, and dTTP or rATP, rCTP, rGTP, and rUTP), and reagents for bisulfite conversion. In some embodiments, the cartridge is part of a kit or system comprising one or more components that introduce these reagents into the wells of the cartridge. In some embodiments, DNA from the patient sample is extracted and applied to the cartridge directly or after bisulfite conversion. In some embodiments, extracted DNA is applied to the cartridge and bisulfite conversion takes place in one or more wells of the cartridge. In some embodiments, the sample is applied directly to the cartridge and, if DNA extraction is needed before bisulfite conversion and amplification, extraction also takes place in one or more wells of the cartridge. In some embodiments, the sample is a urine sample, such as a urine sediment sample (for example comprising urine cell pellets). In other embodiments, the sample is a tissue sample. Thus, in some embodiments, the cartridge is intended to accept either urine or tissue samples. In some embodiments, the cartridge is designed for either urine (e.g. urine sediment) samples or tissue samples. In some embodiments, cartridges and associated systems may be based on those described in International Publication No. WO2006/136990 and its associated U.S. Pat. No. 9,568,424.

In some embodiments, the cartridge comprises at least one well comprising primers where thermocycling takes place as well as one or more wells for introducing, lysing, and/or washing the sample. In some embodiments, the overall cartridge structure also comprises pumps, valves, process wells, and fluid and waste reservoirs, which allow for conducting sample treatment and PCR reactions and associated detection of methylation and optionally also mutation of particular genes in the cartridge.

In some embodiments the cartridge is part of a system that is capable of quantifying methylation of certain genes from the sample using primers and reagents comprised in the cartridge, and the system also includes software capable of quantifying the methylation of the genes and also calculating values based on the methylation, such as sample yield, sample volume, methylation fraction (MF), methylated DNA amount, methylated DNA concentration, Cp values, and an overall Recurrence Score (RS) result. In some embodiments, the system also is capable of creating a report summarizing information such as a subject's MF, methylated DNA amount, and/or methylated DNA concentration, as well as optionally the TERT and/or FGFR3 mutational status. In some embodiments, the system may also compare the quantitative values such as methylated DNA amount and/or methylated DNA concentration with those values taken from reference sets of bladder cancer patients in order to predict risk of recurrence for the patient or detect whether the patient is having an actual recurrence.

Reports

The methods of this invention, when practiced for commercial diagnostic purposes, generally produce a report or summary of information obtained from the herein-described methods. For example, a report may include information concerning amount or concentration of methylated DNA, mutation status of genes, an overall Recurrence Score result for reporting risk of recurrence in comparison to data from a reference set of bladder cancer patients, a prediction of the clinical outcome for a particular patient, or whether the patient is above or below certain recurrence risk thresholds. The methods and reports of this invention can further include storing the report in a database. The method can create a record in a database for the subject and populate the record with data. The report may be a paper report, an auditory report, or an electronic record. The report may be displayed and/or stored on a computing device (e.g., handheld device, desktop computer, smart device, website, etc.). It is contemplated that the report is provided to a physician and/or the patient. The receiving of the report can further include establishing a network connection to a server computer that includes the data and report and requesting the data and report from the server computer.

Computer Programs

The values from the assays described above, such as expression data, recurrence score, treatment score and/or benefit score, can be calculated and stored manually. Alternatively, the above-described steps can be completely or partially performed by a computer program product. The present invention thus provides a computer program product including a computer readable storage medium having a computer program stored on it. The program can, when read by a computer, execute relevant calculations based on values obtained from analysis of one or more biological sample from an individual. The computer program product has stored therein a computer program for performing the calculation.

The present disclosure provides systems for executing the program described above, which system generally includes: a) a central computing environment; b) an input device, operatively connected to the computing environment, to receive patient data, wherein the patient data can include, for example, expression level or other value obtained from an assay using a biological sample from the patient, or microarray data, as described in detail above; c) an output device, connected to the computing environment, to provide information to a user (e.g., medical personnel); and d) an algorithm executed by the central computing environment (e.g., a processor), where the algorithm is executed based on the data received by the input device. The methods provided by the present invention may also be automated in whole or in part.

Having described the invention, the same will be more readily understood through reference to the following Examples, which are provided by way of illustration, and are not intended to limit the invention in any way.

EXAMPLES

Example 1: Methods for Assessing Methylation and Proof of Concept Study

A proof of concept (POC) study was performed using urine cell pellets from 66 bladder cancer patients (25 patients with no recurrence, 14 patients with low risk (LR) (Ta low grade) and 27 patients with high risk (HR) (T1 or high grade)). Recurrence was assessed using 11 methylation gene markers selected based on the literature and 1 methylation-independent (MIP) reference gene. Methylation-specific quantitative PCR (MS-qPCR) analysis preceded by bisulfate conversion was used to determine methylation levels for these 12 genes. This study was used to evaluate the performance of the individual methylation markers and a combined score with respect to predicting the presence of recurrence. Several methods for evaluating methylation signal were developed based on this study and utilized in a refinement study on a larger set of candidate markers.

The methylation fraction (MF) for each gene was estimated from methylation-specific Cp as follows:

First, a linearity study was conducted for each gene by performing a serial dilution of a known concentration of PCR product from amplification of the gene. The product was serial-diluted 2-fold 15 times, and a curve of Cp value at each concentration was prepared and its slope and y-intercept obtained. Second, using the slope and intercept derived from the linearity study, a correction was applied for differential PCR amplification efficiency as follows:

$$m = \frac{C_p(\text{gene}) - \text{intercept (gene)}}{\text{slope (gene)}} \quad \alpha = \frac{C_p(MIP) - MIPintercept}{MIPslope}$$

Third, Cp was normalized using the methylation-independent reference gene data, and MF was estimated according to the equation below:

Methylation Fraction=$2^{m-\alpha}$

Further parameters were then obtained based on the MF, and the DNA yield and volume of the sample, as shown in the table below:

| Method | Calculation per gene | Summary across genes |
|---|---|---|
| Mean Amount of Methylated DNA (ng) | Methylation Fraction × Sample DNA Yield (ng) | Mean |
| Mean Concentration of Methylated DNA (ng/mL) | Methylation Fraction × $\dfrac{\text{Sample DNA Yield (ng)}}{\text{Sample Volume (mL)}}$ | Mean |

A combined score based on 11 genes from the POC study was associated with the presence of recurrence, as shown in the table below.

| Method | Endpoint | Standardized Odds Ratio (95% CI) | p-value |
|---|---|---|---|
| Mean Amount of Methylated DNA (ng) | LR Recurrence | 2.29 (0.98, 5.35) | 0.052 |
| | HR Recurrence | 5.74 (2.37, 13.90) | <.001 |
| Mean Concentration of Methylated DNA (ng/mL) | LR Recurrence | 2.03 (0.93, 4.91) | 0.090 |
| | HR Recurrence | 5.51 (2.52, 14.90) | <.001 |

Example 2: Methylome Discovery Study

A gene discovery study to identify additional gene candidates that are differentially methylated in samples from patients with bladder cancer and those from patients with no cancer was conducted. A total of 26 tumor tissue samples and 7 urine cell pellets from patients with cancer (14 patients previously diagnosed with low risk (LR) of recurrence and 19 patients previously diagnosed with high risk (HR) of recurrence) and 7 urine cell pellets and 5 tissue samples from patients with no cancer (7 healthy individuals and 5 patients with no prior diagnosis of bladder cancer or with prior diagnosis but no malignancy at the time of the surgery) were used in the analysis. Methylome assessment targeted approximately 6 million nucleotides in regions differentially methylated across 11 cancers based on analysis of The Cancer Genome Atlas (TCGA) and sequenced approximately 724,000 sites for each sample. The following assessments were conducted in this discovery study.

First, sites differentially methylated in cancer samples vs. no cancer samples were identified at 1% false discovery rate. Second, strongest candidates for PCR assays for the refinement study were selected based on: (a) regions with strong methylation signal, (b) high coverage, i.e. high number of CpG sites, (c) low signal from non-cancer samples, (d) distribution and location of CpG sites across primers/probes, and (e) areas of consistent methylation signal. Third, based on the findings of the methylome discovery study, 86 candidate methylation markers were taken in the refinement study. This set of 86 candidates included the 11 genes used in the proof of concept study of Example 1.

Example 3: Refinement Study

The refinement study assessed 96 markers including 86 methylation marker genes from the gene discovery study, 4 methylation independent reference genes and 6 FGFR3 mutations on 203 patients with previous diagnosis of bladder cancer who are currently on surveillance. Two of the 6 FGFR3 mutation assays failed to produce any signal and were excluded from further assessments. In addition, 170 patients in this study had enough RNA left for additional assessments, including assaying 2 TERT mutations. The results presented here are based on these 170 patients in which 86 methylation markers, 4 reference genes, 4 FGFR3 and 2 TERT mutations were assessed. The patients included 85 who have not had recurrences, 32 previously diagnosed to have LR recurrence and 53 previously diagnosed to have HR recurrence.

RT-PCR analysis preceded by bisulfate conversion was used to determine methylation levels. The performance of the individual methylation markers was assessed using non-parametric estimates of sensitivity, specificity, negative predictive value (NPV) and positive predictive value (PPV). In this analysis, a positive event for purposes of sensitivity, specificity, NPV, and PPV for a LR recurrence subject was considered to be a prediction of HR recurrence. A positive event for a HR recurrence subject was considered to be evidence of any actual recurrence.

Selection of genes for the final models was based on multiple considerations, including (1) representation of biological pathways, (2) strong individual gene performance with respect to NPV for predicting HR recurrences, (3) consistent selection using elastic net penalized regression models (Zhou H, Hastie T. Regularization and variable selection via the elastic net. *Journal of the Royal Statistical Society*, Series B 67:301-320) for both HR and any recurrence endpoints with and without mutations forced in, (4) strong performance in LASSO penalized regression models (Tibshirani R. Regression shrinkage and selection via the LASSO. *Journal of the Royal Statistical Society*, Series B 58:267-288), and (5) inclusion into POC study. Two main biological pathways were identified: the homeobox functional group was heavily represented (e.g. IRX5, MEIS1, ONECUT2, OTP, POU4F2, SIM2, SOX1), and the immune group (KLF2, IRAK3, ITPKB).

Elastic net analyses identified several genes consistently selected for inclusion in the models with and without including the FGFR3 and TERT mutation assays: KLF2, MEIS1, DDX25, NKPD1, ONECUT2 and TMEM106A. The following table presents genes selected using elastic net analyses.

| HR recurrence vs No Recurrence | | Any recurrence vs No Recurrence | |
|---|---|---|---|
| Methylation assays | Methylation assays + Mutations forced in | Methylation assays | Methylation assays + Mutations forced in |
| KLF2 MEIS1 | KLF2 MEIS1 | KLF2 MEIS1 | KLF2 MEIS1 |

-continued

| HR recurrence vs No Recurrence | | Any recurrence vs No Recurrence | |
| --- | --- | --- | --- |
| Methylation assays | Methylation assays + Mutations forced in | Methylation assays | Methylation assays + Mutations forced in |
| DDX25 | DDX25 | DDX25 | |
| NKPD1 | NKPD1 | NKPD1 | |
| ONECUT2 | ONECUT2 | ONECUT2 | |
| TMEM106A | TMEM106A | TMEM106A | |
| EPHX3 | EPHX3 | | |
| NPR3 | | | |
| SEPT9_P8335 | | | |
| TRPS1_promoter2kb | | | |
| | | IRX5 | IRX5 |
| | | RNF219_AS1 | |
| | | OSR1 | OSR1 |
| | | OTP | |
| | | | KLF1 |
| | | | DKFZp686K1684 |
| | TERT | | TERT |
| | FGFR3 | | FGFR3 |

Thirteen methylation markers selected based on the criteria outlined above were considered for inclusion in the final models. Nine combinations of these methylation markers are described in the table below and were included in final models M1-M9.

| Methylation Assays | M1 | M2 | M3 | M4 | M5 | M6 | M7 | M8 | M9 |
| --- | --- | --- | --- | --- | --- | --- | --- | --- | --- |
| MEIS1* | X | X | X | | X | X | X | | X |
| NKPD1† | X | X | X | | X | X | X | | X |
| ONECUT2†$^{POC}$ | X | X | | X | X | X | X | X | X |
| KLF2*‡$^{b}$ | X | | X | | | X | X | | X |
| OSR1‡¥$^{POC}$ | | X | | | X | X | | | X |
| SOX1†$^{POC}$ | | | X | X | | | | X | X |
| EOMES$^{POC}$ | | | | | X | | | | X |
| TMEM106A†‡ | | | | | X | X | X | | X |
| EPHX3‡ | | | | | X | | | | |
| IRX5¥ | | | | | | X | | | |
| NID2$^{POC}$ | | | | | | | | X | |
| VIM$^{POC}$ | | | | | | | | X | |
| ITPKB$^{b}$ | | | | | | | | | X |

Genes included in the POC study are noted "$^{POC}$" in the table above. The symbol * indicates consistent entry into elastic net-selected models for both HR and Any Rec, with and without mutations.
The symbol † indicates strong performance for NPV as individual gene.
The symbol ‡ indicates strong performance in LASSO models.
The symbol ¥ indicates entry into any recurrence elastic net models.
The symbol $^{b}$ represents immune pathway gene.

In addition to methylation markers, two mutation markers were selected for inclusion. The first is in FGFR3, comprising a C to G mutation at genomic position ch4:1803568, which results in an S249C mutation in the protein. This mutation is found in greater than 65% of patients with low risk, low grade bladder cancer. The limit of detection for this mutation is where Cp=33. The second is in TERT at genomic position chr5:1295228, which is the most prevalent TERT mutation and is found in the promoter region for the gene. The mutation is either a G to A change on one DNA strand or a C to T change on the opposing strand. It is found in about 65% of all bladder cancer patients. The limit of detection for this mutation is where Cp=30. The association signals for presence of each of these mutations with risk of recurrence in low risk and high risk patients is shown in the table below.

| | Proportion of patients with detected mutations by recurrence status | | |
| --- | --- | --- | --- |
| Mutation | No Recurrence | Low Risk Recurrence | High Risk Recurrence |
| FGFR3 | 7% | 25% | 21% |
| TERT | 39% | 50% | 68% |

Addition of the FGFR3 mutation substantially improved prediction of LR recurrence while inclusion of the TERT mutation slightly improved performance for HR recurrence.

Up to four methylation-independent (MIP) reference genes were used and performed well in the linearity studies. The final 2 MIP reference genes COL2A and SLC24A3 were selected based on performance of the model including M1 methylation markers, FGFR3 and TERT mutation assays under four different normalization schemes. No detriment in performance was observed when the number of MIP reference genes was reduced from 4 to 2. Methylation signal was therefore normalized relative to the average of 2 genes: COL2A and SLC24A3.

Performance of each algorithm was evaluated using a multinomial logistic regression model with outcome categories of HR recurrence, LR recurrence and no recurrence, and methylation markers, indicators for the presence of mutations and an indicator variable for initial tumor status (low risk vs high risk) as predictors. Based on this model, the probability of {HR recurrence} and the probability of {LR recurrence} were estimated for every patient in the study population. NPV, PPV, sensitivity and specificity were assessed using model-based estimates of recurrence probabilities, the weighted empirical distribution of predictors in the subgroup (initial high risk or low risk tumor), and the assumed true recurrence prevalence in the target population subgroup, specifically: initial LR tumor patients: 85% no recurrence, 10% LR recurrence, 5% HR recurrence and initial HR tumor patients: 85% no recurrence, 2% LR recurrence, 13% HR recurrence.

Cutpoints for defining presence of HR recurrence were determined at a specific percentiles of the distribution of Pr{HR recurrence} in initial LR patients, for example the $50^{th}$ percentile. Cutpoints for defining presence of any recurrence were determined at a prespecified percentile of the distribution of Pr{Any recurrence} in initial HR patients, for example the $85^{th}$ percentile.

The final algorithms M1-M9 include the following steps:
7) For each of the methylation markers and reference genes, correct for differential PCR amplification efficiency using the intercept and slope estimated from a linearity study:

$$m = \frac{C_p(\text{gene}) - \text{intercept (gene)}}{\text{slope (gene)}} \quad \alpha = \frac{C_p(MIP) - MIPintercept}{MIPslope}$$

8) Calculate average of reference genes mip=average $\alpha$ value of the reference genes
9) Estimate Methylation Fraction for each gene as MF=the maximum of 0 or of (the minimum of 1 or $2^{m-mip}$), i.e. max 0(min 1, $2^{m-mip}$)
10) Apply selected method (a) or (b) to quantify methylation of individual genes:
  a. Amount of methylated DNA amount=MF*Sample yield (ng), or b. Concentration of methylated DNA conc=MF*Sample yield (ng)/Sample Volume (mL)

11) Calculate Log 10 (average amount or conc across the genes)

12) Define presence of mutations in FGFR3 at <33 Cp or TERT at <30 Cp

To evaluate performance of the final algorithms, a multinomial logistic regression model with categories of HR recurrence, LR recurrence and no recurrence was fit with the following predictor variables:

2 degrees of freedom natural cubic spline to the method of choice:

Log 10 (average amount), or

Log 10 (average conc)

Indicators for FGFR3 and TERT mutations

Indicator for patient subgroup (initial LR vs initial HR recurrence).

The performance parameters sensitivity, specificity, negative predictive value (NPV), and positive predictive value (PPV) were estimated using the fitted logistic regression models and assumed true population rates of high risk recurrence and any recurrence for cutoffs ranging from the lowest to the highest estimated recurrence probabilities. (See FIGS. 1-2, 4-5, 7-8, and 10-11 and the Tables below.) Based on the literature and internal studies, in this analysis the following estimates of true population rates of recurrence were used:

1) For initial low risk patients: 85% of patients with no recurrence, 10% of patients with low risk recurrence and 5% of patients with high-risk recurrence 2) For initial high-risk patients: 85% of patients with no recurrence, 2% of patients with low risk recurrence and 13% of patients with high-risk recurrence The performance parameters were plotted against the estimated population quantiles of these probabilities. Additional performance evaluations included (see FIGS. 3, 6, 9, and 12):

1. Predictiveness curves, that is, plots of the estimated probability of HR recurrence or any recurrence against the population quantile of probability 2. ROC curves, that is, plots of the sensitivity versus 1 minus the specificity of a test with cutpoint at each probability of recurrence, and 3. The area under the ROC curve.

Performance of the final models is described in the following tables and in FIGS. 1-12. Model performance of M2-M9 gene combinations is summarized at the percentile cutpoints in the refinement study in the tables below. Specifically, subjects were divided into those with an initial diagnosis of LR recurrence or HR recurrence. For initial LR recurrence subjects, a positive event was considered to be the subject actually falling into the HR recurrence category (endpoint: HR recurrence). For initial HR recurrence subjects, a positive event was considered to be any actual recurrence (endpoint: any recurrence). The table below provides the sensitivity, specificity, NPV, and PPV associated with either HR recurrence in an initial LR subject or any recurrence in an initial HR subject provided at the $50^{th}$ and $85^{th}$ percentiles of the test population.

Figure 1:
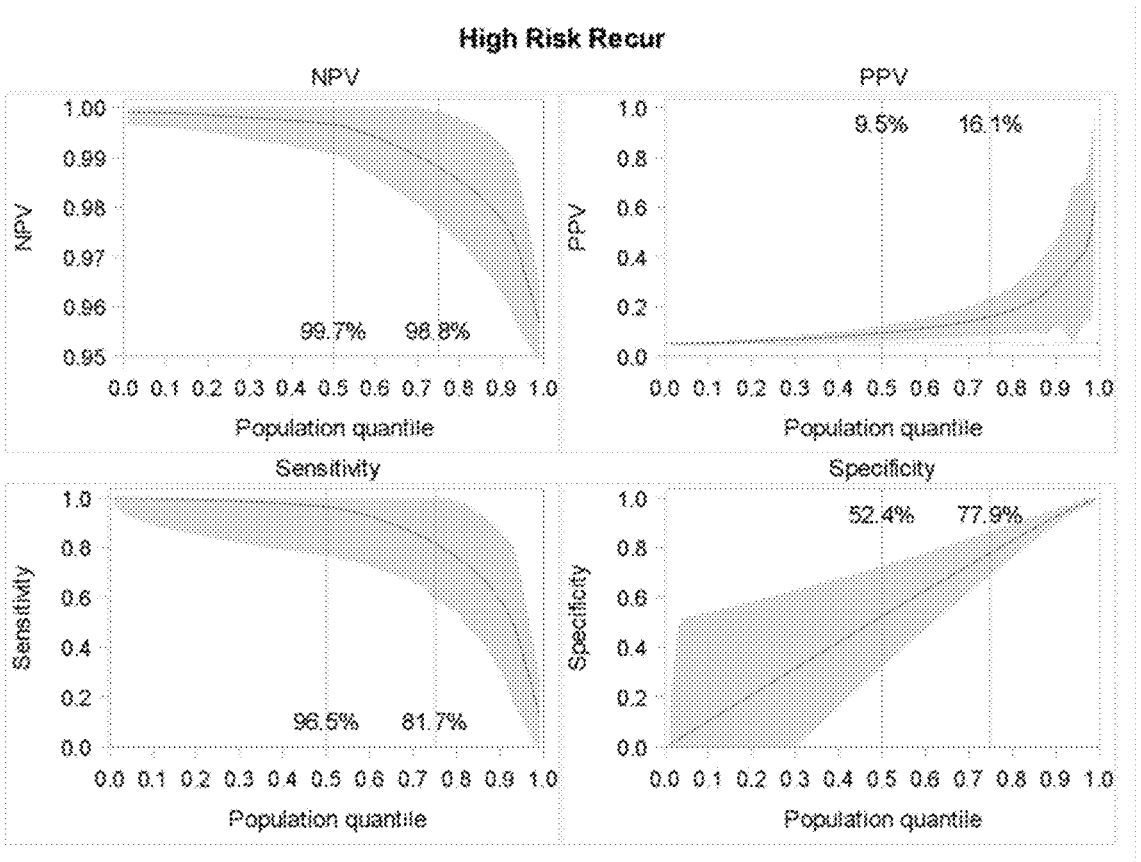
FIG. 1 provides a performance summary for analysis of the amount of methylated DNA for patients who have initially been diagnosed as having a low risk of recurrence ("initial low risk" patients) according to the M1 plus mutation algorithm, as described in Example 3 below. Specifically, FIG. 1 provides negative predictive value (NPV), positive predictive value (PPV), sensitivity, and specificity results for predicting patients in that initial low risk pool who actually are at high risk of recurrence.
Figure 2:
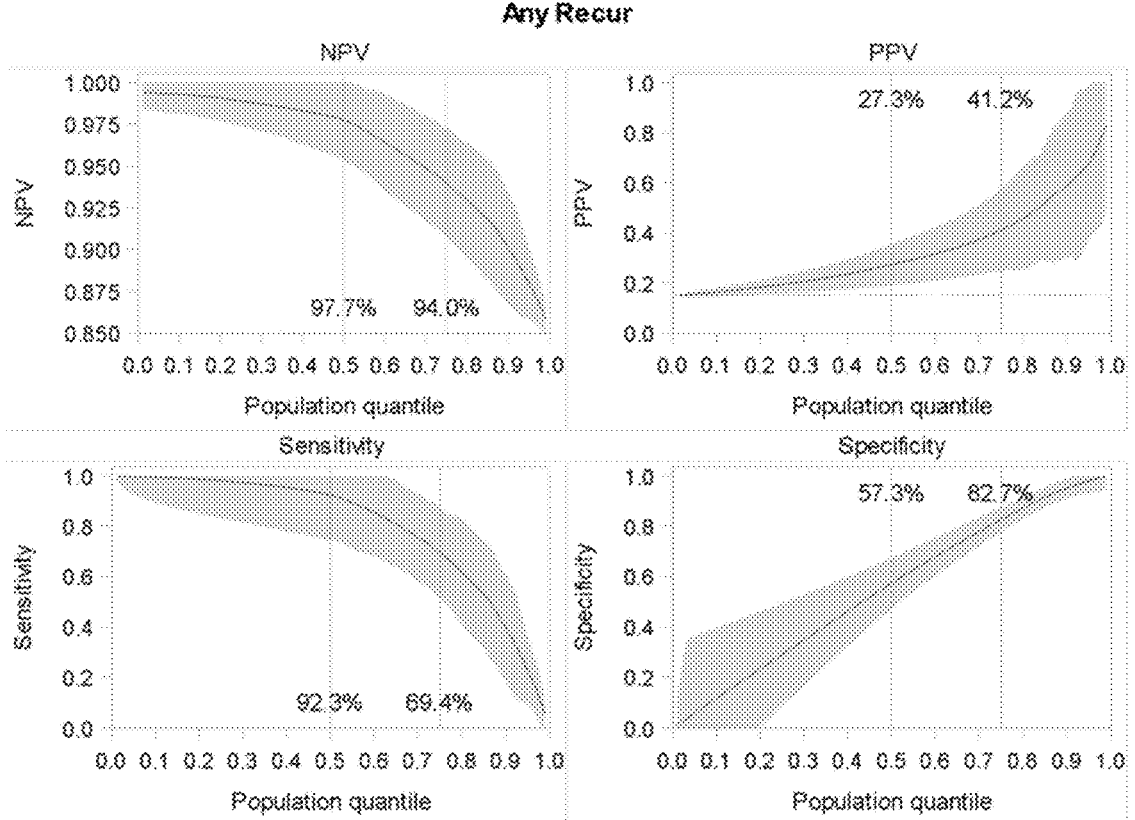
FIG. 2 provides further data of a performance summary for the M1 plus mutation analysis of the amount of methylated DNA for initial low risk of recurrence patients, as described in Example 3 below. Specifically, FIG. 2 provides negative predictive value (NPV), positive predictive value (PPV), sensitivity, and specificity data for predicting those low risk patients who actually have signs of recurrence.
Figure 3:
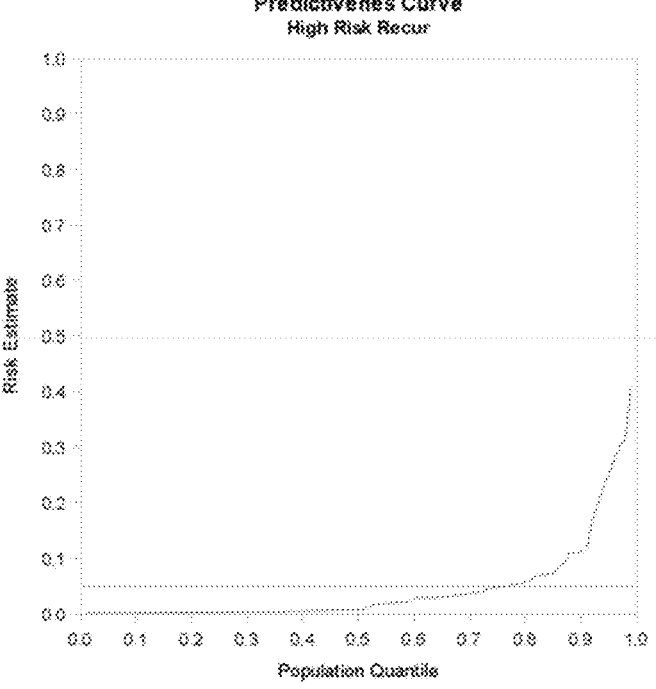
FIG. 3 provides additional data of a performance summary for the M1 plus mutation analysis of the amount of methylated DNA for initial low risk of recurrence patients, as described in Example 3 below. Specifically, FIG. 3 provides predictiveness curves and ROC curves based on the data in FIGS. 1 and 2.
Figure 3:
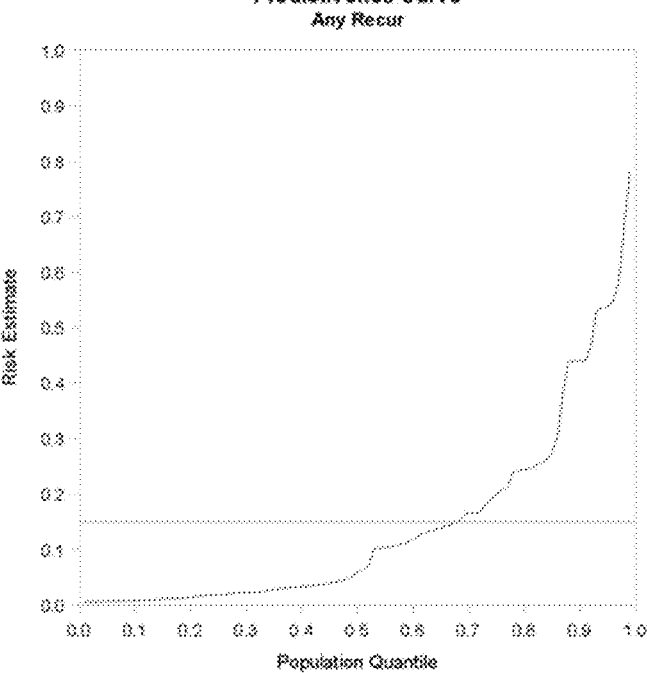
Figure 3:
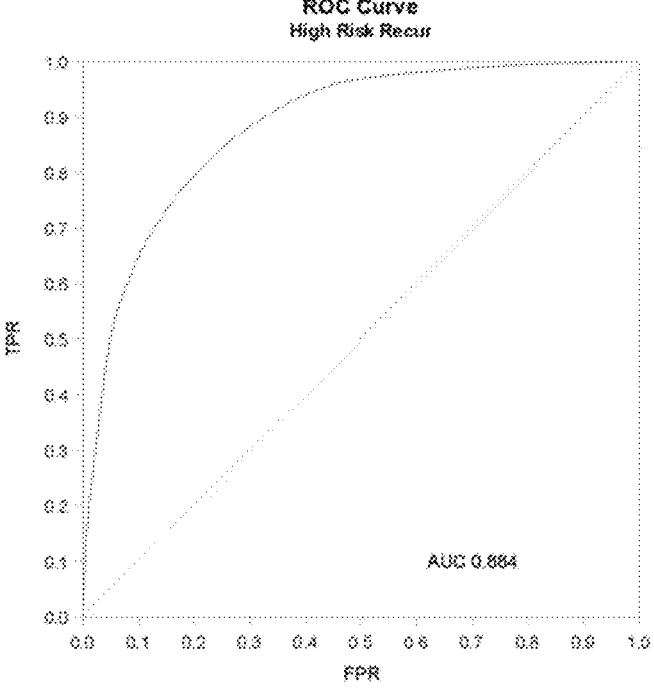
Figure 3:
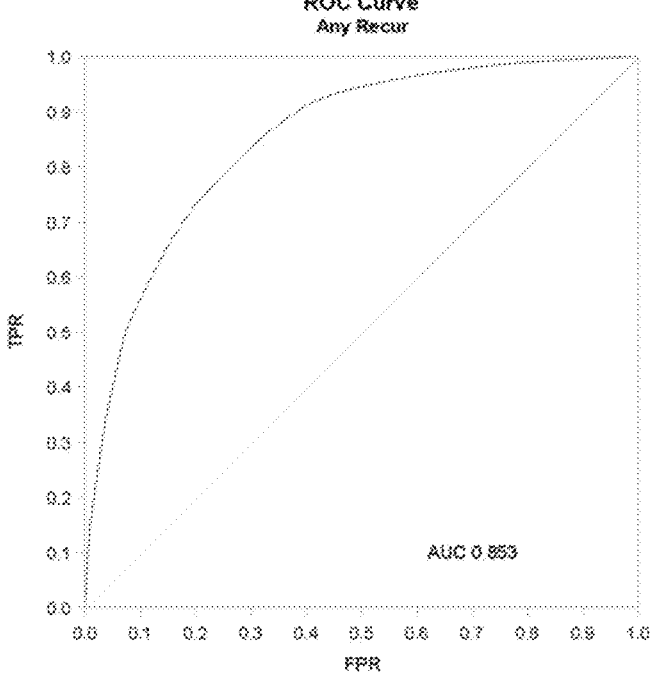
Figure 4:
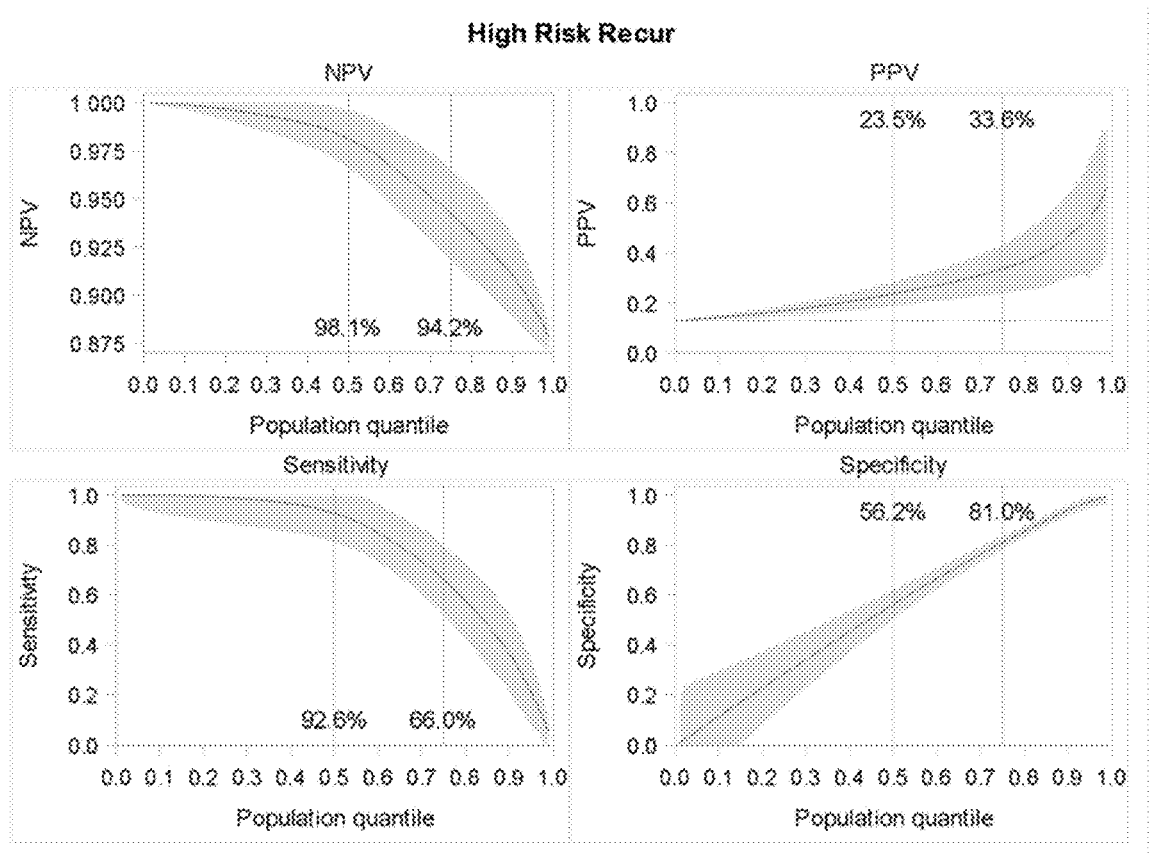
FIG. 4 provides a performance summary for the M1 plus mutation analysis of the amount of methylated DNA for initial low risk of recurrence patients, as described in Example 3 below. Specifically, FIG. 4 provides negative predictive value (NPV), positive predictive value (PPV), sensitivity, and specificity data for predicting those high risk patients who are actually at high risk of recurrence.
Figure 5:
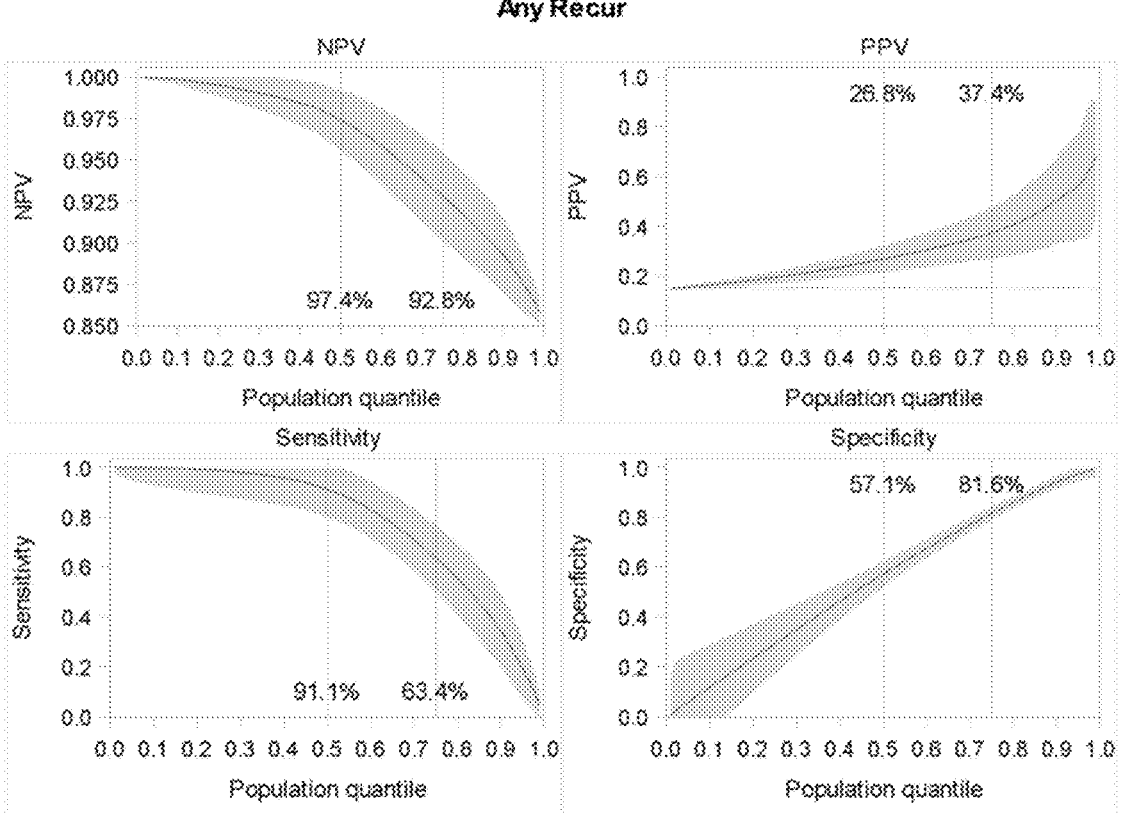
FIG. 5 provides further data of a performance summary for the M1 plus mutation analysis of the amount of methylated DNA for initial low risk of recurrence patients, as described in Example 3 below. Specifically, FIG. 5 provides negative predictive value (NPV), positive predictive value (PPV), sensitivity, and specificity data for predicting those high risk patients who actually have signs of recurrence.
Figure 6:
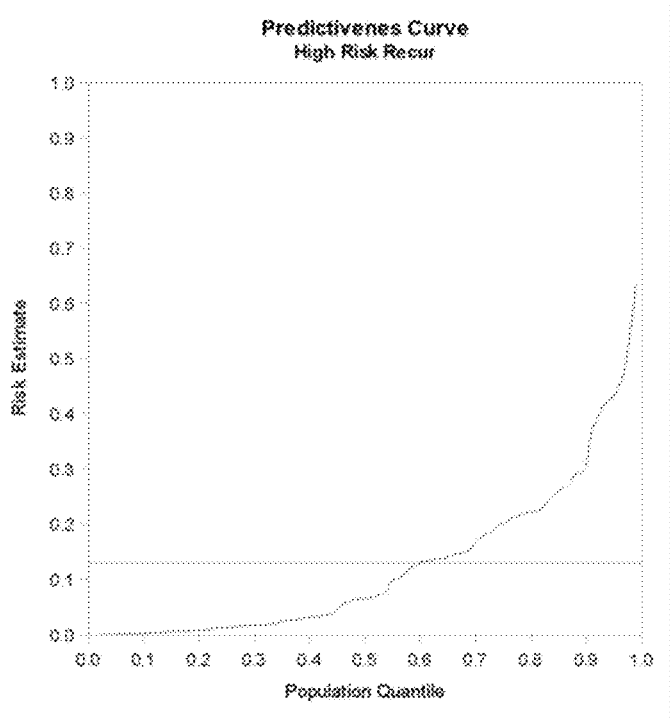
FIG. 6 provides additional data of a performance summary for the M1 plus mutation analysis of the amount of methylated DNA for initial low risk of recurrence patients, as described in Example 3 below. Specifically, FIG. 6 provides predictiveness curves and ROC curves based on the data in FIGS. 4 and 5.
Figure 6:
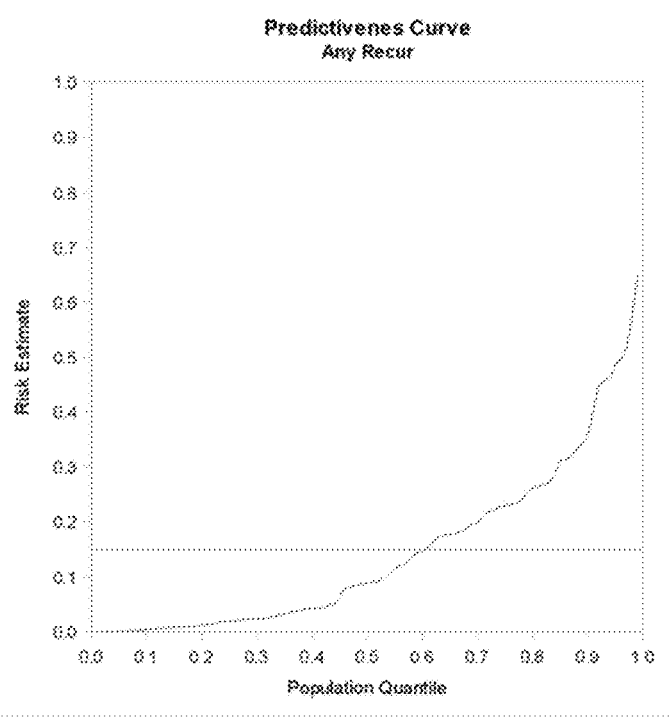
Figure 6:
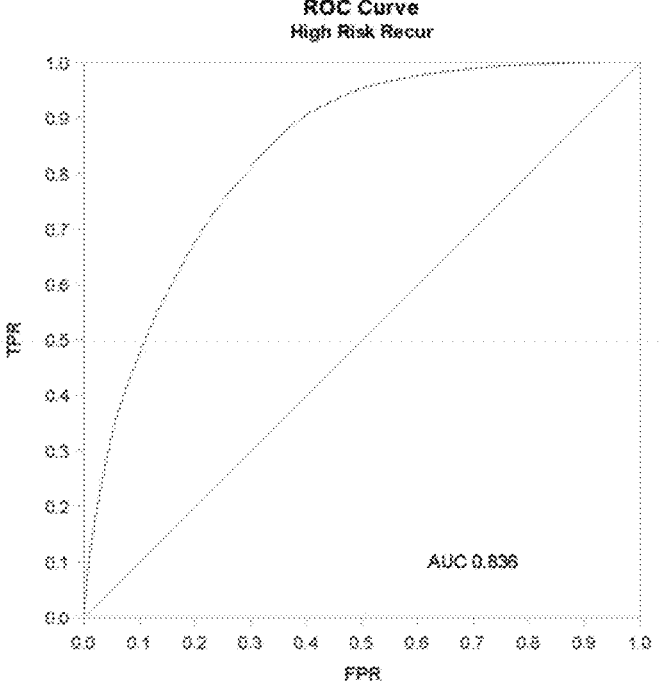
Figure 6:
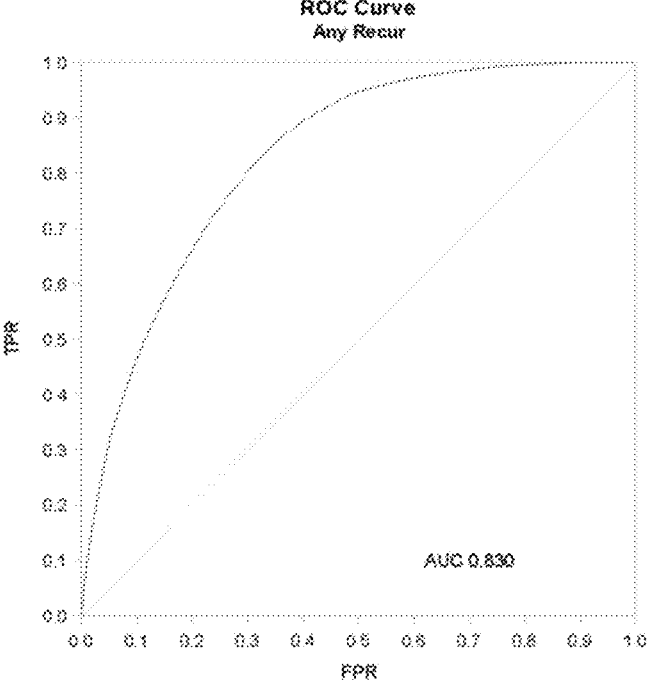

A detailed summary of the performance for the M1 model with the FGFR3 and TERT mutation assays for the amount of methylated DNA and concentration of the methylated DNA is also shown in FIGS. 1-12. For example, FIG. 1 shows the NPV, PPV, sensitivity and specificity curves for initial LR subjects and the NPV, PPV, sensitivity, and specificity values at the $50^{th}$ and $75^{th}$ percentiles of the subjects, where a positive event is considered to be an actual HR of recurrence. FIG. 2 shows the NPV, PPV, sensitivity and specificity curves for initial LR subjects and the NPV, PPV, sensitivity, and specificity values at the $50^{th}$ and $75^{th}$ percentiles of the subjects, where a positive event is considered to be any actual recurrence. Related predictiveness and ROC curves are shown in FIG. 3. Similar data for initial HR patients is shown in FIGS. 4-6. Data based on analysis of the concentration of methylated DNA is shown in FIGS. 7-12.

Performance of the final algorithms M1-M9 for the Amount of Methylated DNA at percentile cutpoints based on the refinement study

| Model | Initial Recurrence | Endpoint | Percentile | Sensitivity | Specificity | NPV | PPV |
|---|---|---|---|---|---|---|---|
| M1 | LR | HR recurrence | 0.50 | 96.5% | 52.4% | 99.7% | 9.5% |
|  |  |  | 0.85 | 69.1% | 87.8% | 98.2% | 22.6% |
|  | HR | Any recurrence | 0.50 | 91.1% | 57.1% | 97.4% | 26.8% |
|  |  |  | 0.85 | 45.7% | 90.3% | 90.6% | 44.8% |
| M2 | LR | HR recurrence | 0.50 | 96.0% | 52.4% | 99.6% | 9.6% |
|  |  |  | 0.85 | 65.2% | 87.6% | 98.0% | 21.9% |
|  | HR | Any recurrence | 0.50 | 90.6% | 57.0% | 97.3% | 26.6% |
|  |  |  | 0.85 | 46.0% | 90.3% | 90.7% | 45.0% |
| M3 | LR | HR recurrence | 0.50 | 96.2% | 52.4% | 99.6% | 9.5% |
|  |  |  | 0.85 | 67.0% | 87.7% | 98.1% | 22.2% |
|  | HR | Any recurrence | 0.50 | 89.9% | 56.9% | 97.1% | 26.4% |
|  |  |  | 0.85 | 45.7% | 90.3% | 90.6% | 44.7% |
| M4 | LR | HR recurrence | 0.50 | 94.2% | 52.3% | 99.4% | 9.1% |
|  |  |  | 0.85 | 61.1% | 87.3% | 97.8% | 19.8% |
|  | HR | Any recurrence | 0.50 | 90.1% | 56.9% | 97.1% | 26.6% |
|  |  |  | 0.85 | 44.9% | 90.2% | 90.5% | 44.1% |
| M5 | LR | HR recurrence | 0.50 | 95.9% | 52.4% | 99.6% | 9.6% |
|  |  |  | 0.85 | 67.0% | 87.7% | 98.1% | 22.3% |
|  | HR | Any recurrence | 0.50 | 90.8% | 57.0% | 97.3% | 26.7% |
|  |  |  | 0.85 | 45.9% | 90.3% | 90.6% | 45.0% |
| M6 | LR | HR recurrence | 0.50 | 96.0% | 52.4% | 99.6% | 9.6% |
|  |  |  | 0.85 | 68.5% | 87.8% | 98.1% | 22.9% |
|  | HR | Any recurrence | 0.50 | 90.6% | 57.0% | 97.2% | 26.6% |
|  |  |  | 0.85 | 46.5% | 90.4% | 90.8% | 45.5% |
| M7 | LR | HR recurrence | 0.50 | 96.0% | 52.4% | 99.6% | 9.5% |
|  |  |  | 0.85 | 68.6% | 87.8% | 98.2% | 22.5% |

-continued

| Model | Initial Recurrence | Endpoint | Percentile | Sensitivity | Specificity | NPV | PPV |
|---|---|---|---|---|---|---|---|
|  | HR | Any recurrence | 0.50 | 90.4% | 57.0% | 97.2% | 26.6% |
|  |  |  | 0.85 | 45.4% | 90.2% | 90.5% | 44.5% |
| M8 | LR | HR recurrence | 0.50 | 93.9% | 52.2% | 99.4% | 8.9% |
|  |  |  | 0.85 | 60.7% | 87.3% | 97.8% | 19.4% |
|  | HR | Any recurrence | 0.50 | 90.0% | 56.9% | 97.0% | 26.6% |
|  |  |  | 0.85 | 44.8% | 90.2% | 90.4% | 44.2% |
| M9 | LR | HR recurrence | 0.50 | 96.3% | 52.4% | 99.6% | 9.5% |
|  |  |  | 0.85 | 69.8% | 87.9% | 98.2% | 23.0% |
|  | HR | Any recurrence | 0.50 | 91.0% | 57.1% | 97.4% | 26.8% |
|  |  |  | 0.85 | 45.2% | 90.2% | 90.5% | 44.4% |

Performance of the Final Algorithms M1-M9 for the Concentration of Methylated DNA at Percentile Cutpoints Based on the Refinement Study

| Model | Initial Recurrence | Endpoint | Percentile | Sensitivity | Specificity | NPV | PPV |
|---|---|---|---|---|---|---|---|
| M1 | LR | HR recurrence | 0.50 | 93.1% | 52.4% | 99.3% | 9.7% |
|  |  |  | 0.85 | 69.0% | 88.0% | 98.1% | 24.0% |
|  | HR | Any recurrence | 0.50 | 89.0% | 56.6% | 96.8% | 25.8% |
|  |  |  | 0.85 | 43.8% | 89.9% | 90.4% | 42.4% |
| M2 | LR | HR recurrence | 0.50 | 93.1% | 52.4% | 99.3% | 9.8% |
|  |  |  | 0.85 | 66.7% | 87.9% | 97.9% | 23.4% |
|  | HR | Any recurrence | 0.50 | 88.5% | 56.5% | 96.7% | 25.6% |
|  |  |  | 0.85 | 44.3% | 90.0% | 90.5% | 42.8% |
| M3 | LR | HR recurrence | 0.50 | 92.7% | 52.4% | 99.2% | 9.7% |
|  |  |  | 0.85 | 66.7% | 87.8% | 98.0% | 23.3% |
|  | HR | Any recurrence | 0.50 | 88.1% | 56.4% | 96.5% | 25.5% |
|  |  |  | 0.85 | 43.4% | 89.8% | 90.4% | 41.8% |
| M4 | LR | HR recurrence | 0.50 | 91.6% | 52.2% | 99.1% | 9.2% |
|  |  |  | 0.85 | 62.8% | 87.5% | 97.8% | 21.2% |
|  | HR | Any recurrence | 0.50 | 87.8% | 56.4% | 96.4% | 25.6% |
|  |  |  | 0.85 | 43.7% | 89.9% | 90.3% | 42.4% |
| M5 | LR | HR recurrence | 0.50 | 93.0% | 52.4% | 99.3% | 9.8% |
|  |  |  | 0.85 | 68.1% | 88.0% | 98.0% | 24.1% |
|  | HR | Any recurrence | 0.50 | 88.8% | 56.6% | 96.8% | 25.8% |
|  |  |  | 0.85 | 44.4% | 90.0% | 90.5% | 43.0% |
| M6 | LR | HR recurrence | 0.50 | 93.1% | 52.4% | 99.3% | 9.9% |
|  |  |  | 0.85 | 68.7% | 88.0% | 98.0% | 24.4% |
|  | HR | Any recurrence | 0.50 | 88.6% | 56.5% | 96.7% | 25.6% |
|  |  |  | 0.85 | 44.4% | 90.0% | 90.5% | 42.8% |
| M7 | LR | HR recurrence | 0.50 | 92.7% | 52.4% | 99.2% | 9.7% |
|  |  |  | 0.85 | 68.1% | 87.9% | 98.0% | 23.9% |
|  | HR | Any recurrence | 0.50 | 88.5% | 56.5% | 96.7% | 25.7% |
|  |  |  | 0.85 | 43.7% | 89.9% | 90.4% | 42.2% |
| M8 | LR | HR recurrence | 0.50 | 91.2% | 52.2% | 99.1% | 9.1% |
|  |  |  | 0.85 | 62.3% | 87.5% | 97.8% | 20.6% |
|  | HR | Any recurrence | 0.50 | 87.6% | 56.4% | 96.4% | 25.6% |
|  |  |  | 0.85 | 43.5% | 89.9% | 90.3% | 42.4% |
| M9 | LR | HR recurrence | 0.50 | 92.9% | 52.4% | 99.2% | 9.8% |
|  |  |  | 0.85 | 69.6% | 88.0% | 98.1% | 24.5% |
|  | HR | Any recurrence | 0.50 | 88.8% | 56.6% | 96.8% | 25.8% |
|  |  |  | 0.85 | 43.7% | 89.9% | 90.4% | 42.2% |

Example 4: Methods for Methylation and Mutation Detection

The following methods have been used for methylation and mutation detection, according to the flow diagram shown in FIG. 13. A Qiagen DNA/RNA MiniKit® was used for DNA extraction from centrifuged urine samples. Bisulfite conversion of the DNA was performed using the Qiagen EpiTect® Fast DNA Bisulfite Kit. Preamplification of the targeted genes and methylation-specific quantitative PCR (MS-qPCR) were performed using a KAPA Probe Fast® kit (KAPA Biosystems).

In the assays, methylation and FGFR3/TERT mutation status were detected in a single workflow assay. This was enabled by bisulfite converting the cell pellet DNA such that methylated cytosines remain cytosines while un-methylated cytosines become uracils, performing a limited number of PCR cycles using methylation specific primers as well as mutation specific primers with wild-type blocking nucleic acids. All of the primers were designed to amplify bisulfite-converted DNA, to anneal to bisulfite-converted templates. This was followed by single-plex quantitative PCR analysis of methylation and mutations on the amplified products to determine the methylation and mutation status of the desired sites. Certain aspects of this methodology are described in J. Morlan et al., *PLoS One* Vol. 4, Issue 2, e4584, pp 1-11 (2009).

Example 5: Validation Study

A clinical validation study of a urine-based assay with genomic and epigenomic markers for predicting recurrence is conducted in non-muscle invasive bladder cancer (NMIBC) subjects. The study will involve about 30 clinical sites and will seek to enroll all patients with an abnormal cystoscopy and cytology at those sites, up to about 380 total patients. Enrollment of 380 patients is expected to yield about 300 usable patient samples for analysis. Specifically, the inclusion criteria are patients with prior diagnosis of non-muscle invasive, T1 or lower, urothelial cell carcinoma of the bladder who are scheduled to undergo surveillance cystoscopy, where the initial diagnosis or most recent recurrence of NMIBC is within the last 5 years. Patients may be excluded if they have muscle invasive disease or are T2 or higher or do not have an available tumor block from their initial diagnosis or most recent recurrence, or who are contraindicated for certain clinical procedures including TURBT.

The primary objective of the study is to validate association between likelihood of recurrence and score results from the methylation assay. The study will also characterize the sensitivity, specificity, NPV and PPV of the assay in this group of patients. Urine samples are collected after first morning void and before any manipulation of the bladder (e.g. cystoscopy, surgery, catheterization) and at least 1 day after a prior manipulation. Archived, fixed, embedded (FPE) tissue samples are also collected from tumor tissue specimens obtained from TURBT, upper GU tract workup, or cystoscopies. The patient's initial cystoscopy, cytology (if available), TURBT or cystoscopy tissue analysis, and upper GU workup are provided. Cystoscopy and cytology are recorded as either normal or abnormal, and tissue from TURBT and upper GU tract workup are recorded as negative, or as Ta low grade, or as high grade, T1-T2, Tis. For purposes of this study, an abnormal cystoscopy result is any abnormality observed that requires a follow-up TURBT, upper GU tract workup or follow-up cystoscopy. An abnormal cytology result is also any abnormality leading to TURBT or upper GU tract workup or follow-up cystoscopy. A positive upper GU tract workup is defined as histologically confirmed upper GU tract urothelial carcinoma while a negative upper GU tract workup is defined as no clinical evidence of an upper GU tract urothelial carcinoma.

The primary clinical endpoint that the test is used to validate is presence of recurrence based on the patient's initial cystoscopy, cytology (if available), TURBT or cystoscopy tissue analysis, and upper GU workup. Generally, patients with a negative tissue analysis result from TURBT or cystoscopy and/or a negative tissue analysis from upper GU tract workup are tested to check that there is no recurrence of cancer. Patients with Ta low grade tissue results from tissue analysis of either TURBT/cystoscopy and/or upper GU tract workup are tested to check that the risk of recurrence is low. Patients with high grade, T1-T2, Tis tissue results from tissue analysis of either TURBT/cystoscopy or upper GU tract workup are tested to check that the risk of recurrence remains high.

Methylation levels of gene markers are measured by quantitative PCR in both FPE samples and urine samples. For each methylation marker, a Cp measurement is obtained and the measurement is normalized relative to a methylation-independent assay from a reference marker. The methylation fraction (MF) from each sample for each gene is calculated as described elsewhere herein.

Statistical analysis will involve about 300 NMIBC patients with bladder cancer methylation analysis results obtained from urine and FPE tissue samples. To obtain this number of samples, the study will enroll about 380 patients. To determine whether there is a significant relationship between the likelihood of recurrence and the methylation analysis result, the analysis will fit a multinomial logistic regression model as described in Example 3 above. A p-value of <0.05 for the likelihood ratio test between the null model excluding the bladder cancer score result and the full model including the bladder cancer score result will be considered significant.

The performance of the methylation analysis at specified cutpoints will be characterized in terms of sensitivity, specificity, negative predictive value (NPV), and positive predictive value (PPV) for predicting any recurrence and separately for predicting high risk of recurrence. These parameters will be calculated based on the logistic regression model noted above with estimates of population prevalence of high risk and low risk recurrence derived from the population screened for study entry.

Multivariate models including bladder cancer methylation analysis and existing risk scoring systems will also be considered, including models with the methylation analysis result and the EORTC, CUETO, and EAU recurrence risk or risk score groups. (See, respectively, R. J. Sylvester et al., *Eur. Urol.* 49: 466-75 (2006); J. Fernandez-Gomez et al., *J. Urol.* 182: 2195-203 (2009); and NCCN Clinical Practice Guidelines in Oncology Bladder Cancer version 2.2015, available at www "dot" nccn "dot" org "/" professionals "/" physician_gls "/" pdf "/" bladder "dot" pdf.)

Additional analyses will include each of the following. First, sensitivity analyses using information from surveillance visits will be conducted. Specifically, patients who had no cancer recurrence in the first on-study surveillance visit but who had a recurrence at a follow-up surveillance visit will be considered as recurrences in the analysis to assess the ability of the methylation assay to detect cancer recurrence early. The performance of the methylation result at particular cutpoint values will be characterized in terms of sensitivity, specificity, NPV, and PPV. Second, the probability of low risk, high risk and any recurrence as a function of methylation analysis result using the multinomial logistic regression model noted above will be estimated by using estimates of population prevalence of high risk and low risk recurrence derived from the population screened for study entry. If the assumptions underlying the logistic model do not hold, alternative techniques may be used to estimate the relationship between the methylation assay result and the likelihood of recurrence and evaluate the sensitivity of the probability estimates to the choice of method. The probability of low risk, high risk and any recurrence will be estimated as a function of the methylation analysis result at various levels of highly prognostic covariates. Alternative functional forms of the association between the methylation score result and likelihood of recurrence using methods such as inclusion of non-linear terms or smoothing splines into the logistic models may also be performed. Third, relationship between methylation test result and probability of recurrence in subgroups defined by prognostic covariates will be evaluated by fitting a multinomial logistic regression model that includes a methylation test result, a given covariate, and the interaction of the two. The model may be adjusted for other highly prognostic variables. Subgroup-specific odds ratios for recurrence may then be reported.

What is claimed is:

1. A method of characterizing a urine sediment sample obtained from a subject, comprising:

bisulfite converting DNA from the sample; and performing methylation-specific quantitative PCR on the bisulfite converted DNA to determine the amount and/or the concentration of methylated DNA in the sample from a set of genes consisting of at least four genes selected from MEIS1, NKPD1, ONECUT2, KLF2, OSR1, SOX1, EOMES, DDX25, TMEM106A, EPHX3, IRX5, NID2, VIM, and ITPKB, wherein the set of genes comprises one or both of NKPD1 and KLF2, and from a set of one or more reference genes, wherein the reference gene(s) have a methylation level that is not significantly different in a subject with bladder cancer compared to a subject without bladder cancer.

2. The method of claim 1, wherein the subject has or is suspected of having bladder cancer.

3. The method of claim 2, wherein the subject has been diagnosed with non-muscle-invasive bladder cancer.

4. The method of claim 2, wherein the sample is obtained from the subject prior to cystoscopy or after a negative cystoscopy.

5. The method of claim 1, wherein the set of genes comprises both of NKPD1 and KLF2.

6. The method of claim 1, wherein the set of one or more reference genes comprises one or more of CTNS, TOP3A, COL2A and SLC24A3.

7. The method of claim 1, wherein the set of genes consists of one of the following gene sets:
  (a) MEIS1, NKPD1, ONECUT2, KLF2;
  (b) MEIS1, NKPD1, ONECUT2, OSR1;
  (c) MEIS1, NKPD1, KLF2, SOX1;
  (d) MEIS1, NKPD1, ONECUT2, OSR1, TMEM106A; EPHX3;
  (e) MEIS1, NKPD1, ONECUT2, KLF2, TMEM106A, IRX5;
  (f) MEIS1, NKPD1, ONECUT2, KLF2, SOX1, TMEM106A; or
  (g) MEIS1, NKPD1, ONECUT2, KLF2, TMEM106A, ITPKB.

8. The method of claim 1, wherein the method further comprises analyzing the bisulfite converted DNA for mutations in one or both of FGFR3 and TERT.

9. The method of claim 1, wherein the set of genes consists of four genes wherein the four genes comprise MEIS1, NKPF1, and KLF2.

10. A method of characterizing a urine sediment sample obtained from a subject, comprising:
  bisulfite converting DNA from the sample; and
  performing methylation-specific quantitative PCR on the bisulfite converted DNA to determine the amount and/or the concentration of methylated DNA in the sample from a set of genes consisting of three or four genes, wherein the set of three or four genes comprises one or both of NKPD1 and KLF2; and from a set of one or more reference genes wherein the reference gene(s) have a methylation level that is not significantly different in a subject with bladder cancer compared to a subject without bladder cancer.

11. The method of claim 10, wherein the subject has or is suspected of having bladder cancer.

12. The method of claim 11, wherein the subject has been diagnosed with non-muscle-invasive bladder cancer.

13. The method of claim 11, wherein the sample is obtained from the patient prior to cystoscopy or after a negative cystoscopy.

14. The method of claim 10, wherein the set of three or four genes consists of (a) one or both of NKPD1 and KLF2 and (b) one, two, or three genes selected from MEIS1, ONECUT2, OSR1, SOX1, EOMES, DDX25, and TMEM106A.

15. The method of claim 10, wherein the set of three or four genes comprises both of NKPD1 and KLF2.

16. The method of claim 10, wherein the set of three or four genes consists of MEIS1, NKPD1, ONECUT2, and KLF2.

17. The method of claim 10, wherein the method further comprises analyzing the bisulfite converted DNA for mutations in one or both of FGFR3 and TERT.

18. The method of claim 10, wherein the set of one or more reference genes comprises one or more of CTNS, TOP3A, COL2A and SLC24A3.

19. The method of claim 10, wherein the set of three or four genes consists of MEIS1, NKPD1, and KLF2.

* * * * *